(12) United States Patent
Kawabata et al.

(10) Patent No.: US 10,709,767 B2
(45) Date of Patent: Jul. 14, 2020

(54) AGENT FOR PROPHYLACTIC AND/OR THERAPEUTIC TREATMENT OF PERIPHERAL NEUROPATHIC PAIN CAUSED BY ANTICANCER AGENT

(71) Applicants: KINKI UNIVERSITY, Higashiosaka-shi, Osaka (JP); ASAHI KASEI PHARMA CORPORATION, Tokyo (JP)

(72) Inventors: Atsufumi Kawabata, Higashiosaka (JP); Hideaki Suzuki, Tokyo (JP)

(73) Assignees: KINKI UNIVERSITY, Osaka (JP); ASAHI KASEI PHARMA CORPORATION, Tokyo (JP)

(*) Notice: Subject to any disclaimer, the term of this patent is extended or adjusted under 35 U.S.C. 154(b) by 0 days.

(21) Appl. No.: 14/404,222

(22) PCT Filed: May 17, 2013

(86) PCT No.: PCT/JP2013/063743
§ 371 (c)(1),
(2) Date: Nov. 26, 2014

(87) PCT Pub. No.: WO2013/179910
PCT Pub. Date: Dec. 5, 2013

(65) Prior Publication Data
US 2015/0148296 A1    May 28, 2015

(30) Foreign Application Priority Data
May 31, 2012  (JP) .................. 2012-125316

(51) Int. Cl.
*A61K 38/36* (2006.01)
*A61K 31/337* (2006.01)
*C07K 14/745* (2006.01)
*A61K 45/06* (2006.01)

(52) U.S. Cl.
CPC .......... *A61K 38/366* (2013.01); *A61K 31/337* (2013.01); *A61K 45/06* (2013.01); *C07K 14/7455* (2013.01)

(58) Field of Classification Search
CPC .................................................. A61K 38/366
See application file for complete search history.

(56) References Cited

U.S. PATENT DOCUMENTS

| | | |
|---|---|---|
| 5,043,425 A | 8/1991 | Aoki et al. |
| 5,516,695 A | 5/1996 | Kim et al. |
| 5,695,964 A | 12/1997 | Nii et al. |
| 5,801,160 A | 9/1998 | Sandage et al. |
| 5,827,832 A | 10/1998 | Sandage, Jr. et al. |
| 5,872,108 A | 2/1999 | Sandage, Jr. et al. |
| 5,916,874 A | 6/1999 | Fujiwara et al. |
| 5,976,523 A | 11/1999 | Awaya et al. |
| 6,034,060 A | 3/2000 | Yamamoto et al. |
| 8,440,832 B2 | 5/2013 | Attala et al. |
| 2002/0111296 A1 | 8/2002 | Festoff et al. |
| 2004/0002446 A1 | 1/2004 | Festoff et al. |
| 2008/0280774 A1* | 11/2008 | Burczynski ...... G01N 33/57426 506/9 |
| 2009/0143281 A1 | 6/2009 | Festoff et al. |
| 2010/0204220 A1 | 8/2010 | Attala et al. |
| 2011/0052723 A1 | 3/2011 | Baeyens-Cabrera et al. |
| 2011/0207803 A1* | 8/2011 | Nabeta .................. A61K 9/107 514/449 |
| 2011/0212900 A1* | 9/2011 | Ikezoe ................ A61K 38/366 514/20.9 |
| 2011/0281876 A1* | 11/2011 | Sun .................... C07D 417/12 514/247 |
| 2011/0287110 A1* | 11/2011 | Dewhirst ............. A61K 31/27 424/649 |
| 2012/0039866 A1* | 2/2012 | Salvemini ........... A61K 31/133 424/130.1 |
| 2013/0237536 A1 | 9/2013 | Attala et al. |

FOREIGN PATENT DOCUMENTS

| | | |
|---|---|---|
| EP | 0312598 A1 | 4/1989 |
| EP | 0356836 A2 | 3/1990 |
| EP | 0489180 A1 | 6/1992 |
| EP | 0743066 A2 | 11/1996 |
| EP | 0763360 A1 | 3/1997 |
| JP | 64-6219 A | 1/1989 |
| JP | 3-86900 A | 4/1991 |
| JP | 8-3065 A | 1/1996 |
| JP | 8-283174 A | 10/1996 |
| JP | 8-301783 A | 11/1996 |
| JP | 9-20677 A | 1/1997 |
| JP | 10-1439 A | 1/1998 |
| JP | 2011-178687 | 9/2011 |
| JP | 2012-1543 A | 1/2012 |
| JP | 6124417 B2 | 4/2017 |

(Continued)

OTHER PUBLICATIONS

Delanian (Radiother Oncol. (2012) 105(3): 273-82).*
Fallon (Br J Anaesth (Jul. 2013) 111(1): 105-111).*
Wen (Biochemistry (1987) 26: 4350-4357).*
Saif et al., 2005, Management of oxaliplatin-induced peripheral neuropathy, Therapeutics and Clinical Risk Management, 1(4): 249-258.*
Damaske et al., 2011, Leucovorin-induced hypersensitivity reaction, Journal of Oncology Pharmacy Practice, 18(1): 136-139.*
Wolf et al., 2008, Chemotherapy-induced peripheral neuropathy: Prevention and treatment strategies, European Journal of Cancer, 44: 1507-1515.*

(Continued)

*Primary Examiner* — Amber D Steele
(74) *Attorney, Agent, or Firm* — Birch, Stewart, Kolasch & Birch, LLP

(57) ABSTRACT

A medicament effective for prophylactic and/or therapeutic treatment of a peripheral neuropathic pain such as allodynia caused by a treatment with an anticancer agent, which comprises thrombomodulin as an active ingredient.

40 Claims, 2 Drawing Sheets
Specification includes a Sequence Listing.

(56) References Cited

FOREIGN PATENT DOCUMENTS

| WO | WO 92/00325 A1 | | 1/1992 | |
|---|---|---|---|---|
| WO | WO 96/22108 A1 | | 7/1996 | |
| WO | WO 96/27380 A1 | | 9/1996 | |
| WO | WO 01/72328 A2 | | 10/2001 | |
| WO | WO 03/061687 | * | 7/2003 | ............ A61K 38/36 |
| WO | WO 2009/103487 A1 | | 8/2009 | |
| WO | WO 2010/006634 A1 | | 1/2010 | |
| WO | WO 2010/006634 A1 | * | 1/2010 | |

OTHER PUBLICATIONS

Abeyama et al., "The N-Terminal domain of thrombomodulin sequesters high-mobility group-B1 protein, a novel antiinflammatory mechanism", The Journal of Clinical Investigation, vol. 115, No. 5, May 2005, pp. 1267-1274.

Dougherty et al., "Taxol-induced sensory disturbance is characterized by preferential impairment of myelinated fiber function in cancer patients", International Association for the Study of Pain, vol. 109, 2004, pp. 132-142.

Egashira et al., "The Current State of the Drugs for Treatment of Peripheral Neuropathy Induced by Anticancer Drugs", Folia Pharmacol. Jpn., vol. 136, 2010, pp. 275-279, with an English translation.

Flatters et al., "Acetyl-L-carnitine prevents and reduces paclitaxel-induced painful peripheral neuropathy", Neuroscience Letters, vol. 397, 2006, pp. 219-223.

Ghelardini et al., "Effects of a New Potent Analog of Tocainide on hNav1.7 Sodium Channels and IN Vivo Neuropathic Pain Models", Neuroscience, vol. 169, 2010, pp. 863-873.

Ikezoe et al., "Successful treatment of sinusoidal obstructive syndrome after hematopoietic stem cell transplantation with recombinant human soluble thrombomodulin", Bone Marrow Transplantation, vol. 45, 2010 (published online Aug. 31, 2009), pp. 783-785.

International Preliminary Report on Patentability and Written Opinion of the International Searching Authority for International Application No. PCT/JP2013/063743 (Forms PCT/IB/338, PCT/IB/373 and PCT/ISA/273) dated Dec. 11, 2014, with English translation.

Ito et al., "Proteolytic Cleavage of High Mobility Group Box 1 Protien by Thrombin-Thrombomodulin Complexes", Arteriosclerosis, Thrombosis, and Vascular Biology, vol. 28, 2008 (published online Jul. 3, 2008), 18 pages.

Jolivalt et al., "Therapeutic efficacy of prosaposin-derived peptide on different models of allodynia", International Association for the Study of Pain, vol. 121, 2006, pp. 14-21.

Otoshi et al., "Anti-HMGB1 Neutralization Antibody Improves Pain-Related Behavior Induced by Application of Autologous Nucleus Pulposus Onto Nerve Roots in Rats", Spine, vol. 36, No. 11, May 2011, pp. E692-E698.

Shibasaki et al., "Induction of high mobility group box-1 in dorsal root ganglion contributes to pain hypersensitivity after peripheral nerve injury", International Association for the Study of Pain, vol. 149, 2010, pp. 514-521.

Shibasaki, "KAKEN-Advances in the Understanding of Mechanisms of Intracellular Signaling by Thrombomodulin in the Hypersensitivity State", FY2010 Annual Report, Dec. 10, 2014, 6 pages.

Smith et al., "Treating Pain from Chemotherapy-induced Peripheral Neuropathy", NCI Cancer Bulletin, vol. 7, No. 4, Feb. 23, 2010, pp. 1-2.

Suzuki et al., Structure and expression of human thrombomodulin, a thrombin receptor on endothelium acting as a cofactor for protein C, The EMBO Journal, vol. 6, No. 7, 1987, pp. 1891-1897.

The 121st Kinki Branch Meeting in Tokushima "Program and Abstracts for the 121st Kinki Branch Meeting of the Japanese Pharmacological Society", The Japanese Pharmacological Society, Jun. 29, 2012, 12 pages.

Chinese Office Action issued in Chinese Patent Application No. 201380028318.4 dated Aug. 5, 2015.

New Zealand Office Action dated Apr. 9, 2015, for New Zealand Application No. 702242.

Australian Office Action for Australian Application No. 2013268725, dated Jul. 15, 2016.

Australian Office Action for Australian Application No. 2013268725, dated Oct. 14, 2016.

Japanese Office Action for Japanese Application No. 2014-518384, dated Sep. 13, 2016, with an English excerpt of the Japanese Office Action.

Tanaka et al., "New Pharmacology," 2002, pp. 568-581, with an English translation.

Australian Examination Report, dated Feb. 2, 2016, for corresponding Australian Application No. 2013268725.

Canadian Office Action, dated Feb. 8, 2016, for corresponding Canadian Application No. 2,875,069.

Extended European Search Report, dated Mar. 8, 2016, for corresponding European Application No. 13796572.9.

Fujii et al., "Calcineurin Inhibitor-Induced Irreversible Neuropathic Pain after Allogeneic Hematopoietic Stem Cell Transplantation," International Journal of Hematology, 2006, vol. 83, pp. 459-461.

Japanese Office Action and English translation thereof, dated Jan. 26, 2016, for corresponding Japanese Application No. 2014-518384.

Korean Office Action issued in Korean Patent Application No. 10-2014-7032155 dated Nov. 13, 2015, with English translation.

New Zealand Office Action issued in New Zealand Patent Application No. 702242 dated Nov. 4, 2015.

Chinese Office Action, dated Apr. 27, 2016, for Chinese Application No. 201380028318.4, with an English translation thereof.

Hafer-Macko et al., "Thrombomodulin Deficiency in Human Diabetic Nerve Microvasculature," Diabetes, vol. 51, Jun. 2002, pp. 1957-1963.

Nurmikko et al., "Sativex successfully treats neuropathic pain characterised by allodynia: A randomised, double-blind, placebo-controlled clinical trial," Pain, vol. 133, 2007, pp. 210-220.

Russian Decision on Grant of Patent for Invention, dated Apr. 27, 2016, for Russian Application No. 2014148171, together with an English translation thereof.

Zhu et al., "Repeated administration of mirtazapine inhibits development of hyperalgesia/allodynia and activation of NF-κB in a rat model of neuropathic pain," Neuroscience Letters, vol. 433, 2008, pp. 33-37.

Candian Office Action, dated Dec. 2, 2016, for Canadian Application No. 2,875,069.

Australian Office Action for Australian Application No. 2013268725, dated Jan. 12, 2017.

Chinese Office Action for Chinese Application No. 201380028318.4, dated Nov. 16, 2016, with an English translation.

English translation of claims of JP6124417B2, Apr. 14, 2017.

Japanese Office Action issued in Japanese Patent Application No. 2017-071200 dated Nov. 14, 2017.

Israeli Office Action issued in corresponding Israeli Application No. 235984 dated Mar. 1, 2018, with an English translation.

Mexican Office Action, dated Nov. 30, 2017, for corresponding Mexican Application No. MX/a/2014/014505, with an English translation.

European Office Action issued in European Patent Application No. 13 796 572.9-1112 dated Mar. 22, 2018.

Vietnamese Office Action for Vietnamese Application No. 1-2014-03964, dated Oct. 17, 2019, with an English transtation.

Mexican Office Action and English summary for Mexican Application No. MX/a/2014/014505, dated Oct. 19, 2018.

Indian Examination Report, dated Jun. 25, 2018, for Indian Application No. 10075/DELNP/2014, with English translation.

Mexican Office Action, dated May 24, 2018, for Mexican Application No. MX/a/2014/014505, with English translation.

Brazilian Office Action for corresponding Brazilian Application No. 112014028852.6, dated Mar. 31, 2020, with partial English translation.

\* cited by examiner

```
                             SEQUENCE LISTING

<160> NUMBER OF SEQ ID NOS: 13

<210> SEQ ID NO 1
<211> LENGTH: 132
<212> TYPE: PRT
<213> ORGANISM: human

<400> SEQUENCE: 1

Met Leu Gly Val Leu Val Leu Gly Ala Leu Ala Leu Ala Gly Leu Gly
1               5                   10                  15

Phe Pro Asp Pro Cys Phe Arg Ala Asn Cys Glu Tyr Gln Cys Gln Pro
                20                  25                  30

Leu Asn Gln Thr Ser Tyr Leu Cys Val Cys Ala Glu Gly Phe Ala Pro
            35                  40                  45

Ile Pro His Glu Pro His Arg Cys Gln Met Phe Cys Asn Gln Thr Ala
        50                  55                  60

Cys Pro Ala Asp Cys Asp Pro Asn Thr Gln Ala Ser Cys Glu Cys Pro
65                  70                  75                  80

Glu Gly Tyr Ile Leu Asp Asp Gly Phe Ile Cys Thr Asp Ile Asp Glu
                85                  90                  95

Cys Glu Asn Gly Gly Phe Cys Ser Gly Val Cys His Asn Leu Pro Gly
                100                 105                 110

Thr Phe Glu Cys Ile Cys Gly Pro Asp Ser Ala Leu Val Arg His Ile
            115                 120                 125

Gly Thr Asp Cys
    130

<210> SEQ ID NO 2
<211> LENGTH: 396
<212> TYPE: DNA
<213> ORGANISM: human

<400> SEQUENCE: 2
atgcttgggg tcctggtcct tggcgcgctg gccctggccg gctgggggtt ccccgacccg     60
tgcttcagag ccaactgcga gtaccagtgc cagcccctga accaaactag ctacctctgc    120
gtctgcgccg agggcttcgc gcccattccc cacgagccgc acaggtgcca gatgttttgc    180
aaccagactg cctgtccagc cgactgcgac cccaacaccc aggctagctg tgagtgcccc    240
gaaggctaca tcctggacga cggtttcatc tgcacggaca tcgacgagtg cgaaaacggc    300
ggcttctgct ccggggtgtg ccacaacctc cccggtacct tcgagtgcat ctgcgggccc    360
gactcggccc ttgtccgcca cattggcacc gactgt                              396

<210> SEQ ID NO 3
<211> LENGTH: 132
<212> TYPE: PRT
<213> ORGANISM: human

<400> SEQUENCE: 3

Met Leu Gly Val Leu Val Leu Gly Ala Leu Ala Leu Ala Gly Leu Gly
1               5                   10                  15

Phe Pro Asp Pro Cys Phe Arg Ala Asn Cys Glu Tyr Gln Cys Gln Pro
                20                  25                  30

Leu Asn Gln Thr Ser Tyr Leu Cys Val Cys Ala Glu Gly Phe Ala Pro
```

```
                35                  40                  45
Ile Pro His Glu Pro His Arg Cys Gln Met Phe Cys Asn Gln Thr Ala
            50                  55                  60
Cys Pro Ala Asp Cys Asp Pro Asn Thr Gln Ala Ser Cys Glu Cys Pro
65                  70                  75                  80
Glu Gly Tyr Ile Leu Asp Asp Gly Phe Ile Cys Thr Asp Ile Asp Glu
                85                  90                  95
Cys Glu Asn Gly Gly Phe Cys Ser Gly Val Cys His Asn Leu Pro Gly
            100                 105                 110
Thr Phe Glu Cys Ile Cys Gly Pro Asp Ser Ala Leu Ala Arg His Ile
        115                 120                 125
Gly Thr Asp Cys
        130

<210> SEQ ID NO 4
<211> LENGTH: 396
<212> TYPE: DNA
<213> ORGANISM: human

<400> SEQUENCE: 4
atgcttgggg tcctggtcct tggcgcgctg gccctggccg gctgggggtt ccccgacccg      60
tgcttcagag ccaactgcga gtaccagtgc cagcccctga accaaactag ctacctctgc     120
gtctgcgccg agggcttcgc gcccattccc acgagccgc acaggtgcca atgttttgc       180 aaccagactg cctgtccagc cgactgcgac cccaacaccc aggctagctg tgagtgccct     240
gaaggctaca tcctggacga cggtttcatc tgcacggaca tcgacgagtg cgaaaacggc     300
ggcttctgct ccggggtgtg ccacaacctc cccggtacct tcgagtgcat ctgcgggccc     360
gactcggccc ttgcccgcca cattggcacc gactgt                               396

<210> SEQ ID NO 5
<211> LENGTH: 480
<212> TYPE: PRT
<213> ORGANISM: human

<400> SEQUENCE: 5

Met Leu Gly Val Leu Val Leu Gly Ala Leu Ala Leu Ala Gly Leu Gly
1               5                   10                  15
Phe Pro Ala Pro Ala Glu Pro Gln Pro Gly Gly Ser Gln Cys Val Glu
            20                  25                  30
His Asp Cys Phe Ala Leu Tyr Pro Gly Pro Ala Thr Phe Leu Asn Ala
        35                  40                  45
Ser Gln Ile Cys Asp Gly Leu Arg Gly His Leu Met Thr Val Arg Ser
    50                  55                  60
Ser Val Ala Ala Asp Val Ile Ser Leu Leu Leu Asn Gly Asp Gly Gly
65                  70                  75                  80
Val Gly Arg Arg Arg Leu Trp Ile Gly Leu Gln Leu Pro Pro Gly Cys
                85                  90                  95
Gly Asp Pro Lys Arg Leu Gly Pro Leu Arg Gly Phe Gln Trp Val Thr
            100                 105                 110
Gly Asp Asn Asn Thr Ser Tyr Ser Arg Trp Ala Arg Leu Asp Leu Asn
        115                 120                 125
Gly Ala Pro Leu Cys Gly Pro Leu Cys Val Ala Val Ser Ala Ala Glu
    130                 135                 140
Ala Thr Val Pro Ser Glu Pro Ile Trp Glu Glu Gln Gln Cys Glu Val
145                 150                 155                 160
```

```
Lys Ala Asp Gly Phe Leu Cys Glu Phe His Phe Pro Ala Thr Cys Arg
            165                 170                 175
Pro Leu Ala Val Glu Pro Gly Ala Ala Ala Ala Val Ser Ile Thr
        180                 185                 190
Tyr Gly Thr Pro Phe Ala Ala Arg Gly Ala Asp Phe Gln Ala Leu Pro
        195                 200                 205
Val Gly Ser Ser Ala Ala Val Ala Pro Leu Gly Leu Gln Leu Met Cys
    210                 215                 220
Thr Ala Pro Pro Gly Ala Val Gln Gly His Trp Ala Arg Glu Ala Pro
225                 230                 235                 240
Gly Ala Trp Asp Cys Ser Val Glu Asn Gly Cys Glu His Ala Cys
            245                 250                 255
Asn Ala Ile Pro Gly Ala Pro Arg Cys Gln Cys Pro Ala Gly Ala Ala
            260                 265                 270
Leu Gln Ala Asp Gly Arg Ser Cys Thr Ala Ser Ala Thr Gln Ser Cys
    275                 280                 285
Asn Asp Leu Cys Glu His Phe Cys Val Pro Asn Pro Asp Gln Pro Gly
    290                 295                 300
Ser Tyr Ser Cys Met Cys Glu Thr Gly Tyr Arg Leu Ala Ala Asp Gln
305                 310                 315                 320
His Arg Cys Glu Asp Val Asp Cys Ile Leu Glu Pro Ser Pro Cys
            325                 330                 335
Pro Gln Arg Cys Val Asn Thr Gln Gly Gly Phe Glu Cys His Cys Tyr
            340                 345                 350
Pro Asn Tyr Asp Leu Val Asp Gly Glu Cys Val Glu Pro Val Asp Pro
            355                 360                 365
Cys Phe Arg Ala Asn Cys Glu Tyr Gln Cys Gln Pro Leu Asn Gln Thr
    370                 375                 380
Ser Tyr Leu Cys Val Cys Ala Glu Gly Phe Ala Pro Ile Pro His Glu
385                 390                 395                 400
Pro His Arg Cys Gln Met Phe Cys Asn Gln Thr Ala Cys Pro Ala Asp
            405                 410                 415
Cys Asp Pro Asn Thr Gln Ala Ser Cys Glu Cys Pro Glu Gly Tyr Ile
            420                 425                 430
Leu Asp Asp Gly Phe Ile Cys Thr Asp Ile Asp Glu Cys Glu Asn Gly
            435                 440                 445
Gly Phe Cys Ser Gly Val Cys His Asn Leu Pro Gly Thr Phe Glu Cys
    450                 455                 460
Ile Cys Gly Pro Asp Ser Ala Leu Val Arg His Ile Gly Thr Asp Cys
465                 470                 475                 480

<210> SEQ ID NO 6
<211> LENGTH: 1440
<212> TYPE: DNA
<213> ORGANISM: human

<400> SEQUENCE: 6
atgcttgggg tcctggtcct tggcgcgctg gccctggccg gcctgggggtt ccccgcaccc      60 gcagagccgc agccgggtgg cagccagtgc gtcgagcacg actgcttcgc gctctacccg     120
ggccccgcga ccttcctcaa tgccagtcag atctgcgacg gactgcgggg ccacctaatg     180
acagtgcgct cctcggtggc tgccgatgtc atttccttgc tactgaacgg cgacggcggc     240
gttggccgcc ggcgcctctg gatcggcctg cagctgccac ccggctgcgg cgaccccaag     300
```

```
cgcctcgggc ccctgcgcgg cttccagtgg gttacgggag acaacaacac cagctatagc      360
aggtgggcac ggctcgacct caatggggct ccctctgcg gccgttgtg cgtcgctgtc       420 tccgctgctg aggccactgt gcccagcgag ccgatctggg aggagcagca gtgcgaagtg      480
aaggccgatg gcttcctctg cgagttccac ttcccagcca cctgcaggcc actggctgtg      540
gagcccggcg ccgcggctgc cgccgtctcg atcacctacg caccccgtt cgcggcccgc       600 ggagcggact ccaggcgct gccggtgggc agctccgccg cggtggctcc cctcggctta      660
cagctaatgt gcaccgcgcc gcccggagcg gtccaggggc actgggccag ggaggcgccg      720
ggcgcttggg actgcagcgt ggagaacggc ggctgcgagc acgcgtgcaa tgcgatccct      780
ggggctcccc gctgccagtg cccagccggc gccgccctgc aggcagacgg cgctcctgc       840 accgcatccg cgacgcagtc ctgcaacgac ctctgcgagc acttctgcgt tcccaacccc      900
gaccagccgg gctcctactc gtgcatgtgc gagaccggct accggctggc ggccgaccaa      960
caccggtgcg aggacgtgga tgactgcata ctggagccca gtccgtgtcc gcagcgctgt     1020
gtcaacacac agggtggctt cgagtgccac tgctacccta actacgacct ggtggacggc     1080
gagtgtgtgg agcccgtgga cccgtgcttc agagccaact gcgagtacca gtgccagccc     1140
ctgaaccaaa ctagctacct ctgcgtctgc gccgagggct cgcgcccat tccccacgag     1200 ccgcacaggt gccagatgtt ttgcaaccag actgcctgtc cagccgactg cgaccccaac     1260
acccaggcta gctgtgagtg ccctgaaggc tacatcctgg acgacggttt catctgcacg     1320
gacatcgacg agtgcgaaaa cggcggcttc tgctccgggg tgtgccacaa cctccccggt     1380
accttcgagt gcatctgcgg gcccgactcg gcccttgtcc gccacattgg caccgactgt     1440
```

<210> SEQ ID NO 7
<211> LENGTH: 480
<212> TYPE: PRT
<213> ORGANISM: human

<400> SEQUENCE: 7

```
Met Leu Gly Val Leu Val Leu Gly Ala Leu Ala Leu Ala Gly Leu Gly
1               5                   10                  15

Phe Pro Ala Pro Ala Glu Pro Gln Pro Gly Gly Ser Gln Cys Val Glu
                20                  25                  30

His Asp Cys Phe Ala Leu Tyr Pro Gly Pro Ala Thr Phe Leu Asn Ala
            35                  40                  45

Ser Gln Ile Cys Asp Gly Leu Arg Gly His Leu Met Thr Val Arg Ser
        50                  55                  60

Ser Val Ala Ala Asp Val Ile Ser Leu Leu Leu Asn Gly Asp Gly Gly
65                  70                  75                  80

Val Gly Arg Arg Arg Leu Trp Ile Gly Leu Gln Leu Pro Pro Gly Cys
                85                  90                  95

Gly Asp Pro Lys Arg Leu Gly Pro Leu Arg Gly Phe Gln Trp Val Thr
                100                 105                 110

Gly Asp Asn Asn Thr Ser Tyr Ser Arg Trp Ala Arg Leu Asp Leu Asn
            115                 120                 125

Gly Ala Pro Leu Cys Gly Pro Leu Cys Val Ala Val Ser Ala Ala Glu
        130                 135                 140

Ala Thr Val Pro Ser Glu Pro Ile Trp Glu Glu Gln Gln Cys Glu Val
145                 150                 155                 160

Lys Ala Asp Gly Phe Leu Cys Glu Phe His Phe Pro Ala Thr Cys Arg
                165                 170                 175
```

```
Pro Leu Ala Val Glu Pro Gly Ala Ala Ala Ala Val Ser Ile Thr
            180                 185                 190
Tyr Gly Thr Pro Phe Ala Ala Arg Gly Ala Asp Phe Gln Ala Leu Pro
        195                 200                 205
Val Gly Ser Ser Ala Ala Val Ala Pro Leu Gly Leu Gln Leu Met Cys
    210                 215                 220
Thr Ala Pro Pro Gly Ala Val Gln His Trp Ala Arg Glu Ala Pro
225                 230                 235                 240
Gly Ala Trp Asp Cys Ser Val Glu Asn Gly Cys Glu His Ala Cys
                245                 250                 255
Asn Ala Ile Pro Gly Ala Pro Arg Cys Gln Cys Pro Ala Gly Ala Ala
            260                 265                 270
Leu Gln Ala Asp Gly Arg Ser Cys Thr Ala Ser Ala Thr Gln Ser Cys
        275                 280                 285
Asn Asp Leu Cys Glu His Phe Cys Val Pro Asn Pro Asp Gln Pro Gly
    290                 295                 300
Ser Tyr Ser Cys Met Cys Glu Thr Gly Tyr Arg Leu Ala Ala Asp Gln
305                 310                 315                 320
His Arg Cys Glu Asp Val Asp Asp Cys Ile Leu Glu Pro Ser Pro Cys
                325                 330                 335
Pro Gln Arg Cys Val Asn Thr Gln Gly Gly Phe Glu Cys His Cys Tyr
            340                 345                 350
Pro Asn Tyr Asp Leu Val Asp Gly Glu Cys Val Glu Pro Val Asp Pro
        355                 360                 365
Cys Phe Arg Ala Asn Cys Glu Tyr Gln Cys Gln Pro Leu Asn Gln Thr
    370                 375                 380
Ser Tyr Leu Cys Val Cys Ala Glu Gly Phe Ala Pro Ile Pro His Glu
385                 390                 395                 400
Pro His Arg Cys Gln Met Phe Cys Asn Gln Thr Ala Cys Pro Ala Asp
                405                 410                 415
Cys Asp Pro Asn Thr Gln Ala Ser Cys Glu Cys Pro Glu Gly Tyr Ile
            420                 425                 430
Leu Asp Asp Gly Phe Ile Cys Thr Asp Ile Asp Glu Cys Glu Asn Gly
        435                 440                 445
Gly Phe Cys Ser Gly Val Cys His Asn Leu Pro Gly Thr Phe Glu Cys
    450                 455                 460
Ile Cys Gly Pro Asp Ser Ala Leu Ala Arg His Ile Gly Thr Asp Cys
465                 470                 475                 480

<210> SEQ ID NO 8
<211> LENGTH: 1440
<212> TYPE: DNA
<213> ORGANISM: human

<400> SEQUENCE: 8
atgcttgggg tcctggtcct tggcgcgctg gccctggccg gctgggggtt ccccgcaccc      60
gcagagccgc agccgggtgg cagccagtgc gtcgagcacg actgcttcgc gctctacccg     120
ggccccgcga ccttcctcaa tgccagtcag atctgcgacg gactgcgggg ccacctaatg     180
acagtgcgct cctcggtggc tgccgatgtc atttccttgc tactgaacgg cgacggcggc     240
gttggccgcc ggcgcctctg gatcggcctg cagctgccac ccggctgcgg cgaccccaag     300
cgcctcgggc cctgcgcgg cttccagtgg ggttacggga gacaacaacac cagctatagc     360 aggtgggcac ggctcgacct caatgggggct ccctctgcg gcccgttgtg cgtcgctgtc     420
```

```
tccgctgctg aggccactgt gcccagcgag ccgatctggg aggagcagca gtgcgaagtg      480
aaggccgatg gcttcctctg cgagttccac ttcccagcca cctgcaggcc actggctgtg      540
gagcccggcg ccgcggctgc cgccgtctcg atcacctacg gcaccccgtt cgcggcccgc      600
ggagcggact ccaggcgct gccggtgggc agctccgccg cggtggctcc cctcggctta      660
cagctaatgt gcaccgcgcc gcccggagcg gtccaggggc actgggccag ggaggcgccg      720
ggcgcttggg actgcagcgt ggagaacggc ggctgcgagc acgcgtgcaa tgcgatccct      780
ggggctcccc gctgccagtg cccagccggc gccgccctgc aggcagacgg cgctcctgc       840
accgcatccg cgacgcagtc ctgcaacgac ctctgcgagc acttctgcgt tcccaacccc      900
gaccagccgg gctcctactc gtgcatgtgc gagaccggct accggctggc ggccgaccaa      960
caccggtgcg aggacgtgga tgactgcata ctggagccca gtccgtgtcc gcagcgctgt     1020
gtcaacacac agggtggctt cgagtgccac tgctacccta actacgacct ggtggacggc     1080
gagtgtgtgg agcccgtgga cccgtgcttc agagccaact gcgagtacca gtgccagccc     1140
ctgaaccaaa ctagctacct ctgcgtctgc ccgagggct tcgcgcccat tccccacgag      1200
ccgcacaggt gccagatgtt ttgcaaccag actgcctgtc cagccgactg cgaccccaac     1260
acccaggcta gctgtgagtg ccctgaaggc tacatcctgg acgacggttt catctgcacg     1320
gacatcgacg agtgcgaaaa cggcggcttc tgctccgggg tgtgccacaa cctccccggt     1380
accttcgagt gcatctgcgg gcccgactcg gcccttgccc gccacattgg caccgactgt     1440
```

<210> SEQ ID NO 9
<211> LENGTH: 516
<212> TYPE: PRT
<213> ORGANISM: human

<400> SEQUENCE: 9

Met Leu Gly Val Leu Val Leu Gly Ala Leu Ala Leu Ala Gly Leu Gly
1               5                   10                  15

Phe Pro Ala Pro Ala Glu Pro Gln Pro Gly Gly Ser Gln Cys Val Glu
            20                  25                  30

His Asp Cys Phe Ala Leu Tyr Pro Gly Pro Ala Thr Phe Leu Asn Ala
        35                  40                  45

Ser Gln Ile Cys Asp Gly Leu Arg Gly His Leu Met Thr Val Arg Ser
    50                  55                  60

Ser Val Ala Ala Asp Val Ile Ser Leu Leu Leu Asn Gly Asp Gly Gly
65                  70                  75                  80

Val Gly Arg Arg Arg Leu Trp Ile Gly Leu Gln Leu Pro Pro Gly Cys
                85                  90                  95

Gly Asp Pro Lys Arg Leu Gly Pro Leu Arg Gly Phe Gln Trp Val Thr
            100                 105                 110

Gly Asp Asn Asn Thr Ser Tyr Ser Arg Trp Ala Arg Leu Asp Leu Asn
        115                 120                 125

Gly Ala Pro Leu Cys Gly Pro Leu Cys Val Ala Val Ser Ala Ala Glu
    130                 135                 140

Ala Thr Val Pro Ser Glu Pro Ile Trp Glu Glu Gln Gln Cys Glu Val
145                 150                 155                 160

Lys Ala Asp Gly Phe Leu Cys Glu Phe His Phe Pro Ala Thr Cys Arg
                165                 170                 175

Pro Leu Ala Val Glu Pro Gly Ala Ala Ala Ala Val Ser Ile Thr
            180                 185                 190

Tyr Gly Thr Pro Phe Ala Ala Arg Gly Ala Asp Phe Gln Ala Leu Pro

|  |  |  | 195 |  |  |  | 200 |  |  |  | 205 |  |
|---|---|---|---|---|---|---|---|---|---|---|---|---|

Val Gly Ser Ser Ala Ala Val Ala Pro Leu Gly Leu Gln Leu Met Cys
210                215                220

Thr Ala Pro Pro Gly Ala Val Gln Gly His Trp Ala Arg Glu Ala Pro
225                230                235                240

Gly Ala Trp Asp Cys Ser Val Glu Asn Gly Cys Glu His Ala Cys
                245                250                255

Asn Ala Ile Pro Gly Ala Pro Arg Cys Gln Cys Pro Ala Gly Ala Ala
                260                265                270

Leu Gln Ala Asp Gly Arg Ser Cys Thr Ala Ser Ala Thr Gln Ser Cys
                275                280                285

Asn Asp Leu Cys Glu His Phe Cys Val Pro Asn Pro Asp Gln Pro Gly
                290                295                300

Ser Tyr Ser Cys Met Cys Glu Thr Gly Tyr Arg Leu Ala Ala Asp Gln
305                310                315                320

His Arg Cys Glu Asp Val Asp Asp Cys Ile Leu Glu Pro Ser Pro Cys
                325                330                335

Pro Gln Arg Cys Val Asn Thr Gln Gly Gly Phe Glu Cys His Cys Tyr
                340                345                350

Pro Asn Tyr Asp Leu Val Asp Gly Glu Cys Val Glu Pro Val Asp Pro
                355                360                365

Cys Phe Arg Ala Asn Cys Glu Tyr Gln Cys Gln Pro Leu Asn Gln Thr
370                375                380

Ser Tyr Leu Cys Val Cys Ala Glu Gly Phe Ala Pro Ile Pro His Glu
385                390                395                400

Pro His Arg Cys Gln Met Phe Cys Asn Gln Thr Ala Cys Pro Ala Asp
                405                410                415

Cys Asp Pro Asn Thr Gln Ala Ser Cys Glu Cys Pro Glu Gly Tyr Ile
                420                425                430

Leu Asp Asp Gly Phe Ile Cys Thr Asp Ile Asp Glu Cys Glu Asn Gly
                435                440                445

Gly Phe Cys Ser Gly Val Cys His Asn Leu Pro Gly Thr Phe Glu Cys
                450                455                460

Ile Cys Gly Pro Asp Ser Ala Leu Val Arg His Ile Gly Thr Asp Cys
465                470                475                480

Asp Ser Gly Lys Val Asp Gly Gly Asp Ser Gly Ser Gly Glu Pro Pro
                485                490                495

Pro Ser Pro Thr Pro Gly Ser Thr Leu Thr Pro Pro Ala Val Gly Leu
                500                505                510

Val His Ser Gly
        515

<210> SEQ ID NO 10
<211> LENGTH: 1548
<212> TYPE: DNA
<213> ORGANISM: human

<400> SEQUENCE: 10

```
atgcttgggg tcctggtcct tggcgcgctg gccctggccg gctgggggtt ccccgcaccc      60
gcagagccgc agccgggtgg cagccagtgc gtcgagcacg actgcttcgc gctctacccg     120
ggccccgcga ccttcctcaa tgccagtcag atctgcgacg gactgcgggg ccacctaatg     180
acagtgcgct cctcggtggc tgccgatgtc atttccttgc tactgaacgg cgacggcggc     240
gttggccgcc ggcgcctctg gatcggcctg cagctgccac ccggctgcgg cgaccccaag     300
```

-continued

```
cgcctcgggc ccctgcgcgg cttccagtgg gttacgggag acaacaacac cagctatagc    360
aggtgggcac ggctcgacct caatggggct cccctctgcg gcccgttgtg cgtcgctgtc    420
tccgctgctg aggccactgt gcccagcgag ccgatctggg aggagcagca gtgcgaagtg    480
aaggccgatg gcttcctctg cgagttccac ttcccagcca cctgcaggcc actggctgtg    540
gagcccggcg ccgcggctgc cgccgtctcg atcacctacg caccccgtt cgcggcccgc     600
ggagcggact ccaggcgct gccggtgggc agctccgccg cggtggctcc cctcggctta     660
cagctaatgt gcaccgcgcc gcccggagcg gtccaggggc actgggccag ggaggcgccg    720
ggcgcttggg actgcagcgt ggagaacggc ggctgcgagc acgcgtgcaa tgcgatccct    780
ggggctcccc gctgccagtg cccagccggc gccgccctgc aggcagacgg gcgctcctgc    840
accgcatccg cgacgcagtc ctgcaacgac ctctgcgagc acttctgcgt tcccaacccc    900
gaccagccgg gctcctactc gtgcatgtgc gagaccggct accggctggc ggccgaccaa    960
caccggtgcg aggacgtgga tgactgcata ctggagccca gtccgtgtcc gcagcgctgt   1020
gtcaacacac agggtggctt cgagtgccac tgctacccta actacgacct ggtggacggc   1080
gagtgtgtgg agcccgtgga cccgtgcttc agagccaact gcgagtacca gtgccagccc   1140
ctgaaccaaa ctagctacct ctgcgtctgc gccgagggct cgcgcccat tccccacgag    1200
ccgcacaggt gccagatgtt ttgcaaccag actgcctgtc cagccgactg cgaccccaac   1260
acccaggcta gctgtgagtg ccctgaaggc tacatcctgg acgacggttt catctgcacg   1320
gacatcgacg agtgcgaaaa cggcggcttc tgctccgggg tgtgccacaa cctcccggt    1380
accttcgagt gcatctgcgg gcccgactcg gcccttgtcc gccacattgg caccgactgt   1440
gactccggca aggtgacgg tggcgacagc ggctctggcg agccccgcc cagcccgacg    1500
cccggctcca ccttgactcc tccggccgtg gggctcgtgc attcgggc                1548
```

<210> SEQ ID NO 11
<211> LENGTH: 516
<212> TYPE: PRT
<213> ORGANISM: human

<400> SEQUENCE: 11

```
Met Leu Gly Val Leu Val Leu Gly Ala Leu Ala Leu Ala Gly Leu Gly
1               5                   10                  15

Phe Pro Ala Pro Ala Glu Pro Gln Pro Gly Gly Ser Gln Cys Val Glu
                20                  25                  30

His Asp Cys Phe Ala Leu Tyr Pro Gly Pro Ala Thr Phe Leu Asn Ala
            35                  40                  45

Ser Gln Ile Cys Asp Gly Leu Arg Gly His Leu Met Thr Val Arg Ser
        50                  55                  60

Ser Val Ala Ala Asp Val Ile Ser Leu Leu Leu Asn Gly Asp Gly Gly
65                  70                  75                  80

Val Gly Arg Arg Arg Leu Trp Ile Gly Leu Gln Leu Pro Pro Gly Cys
                85                  90                  95

Gly Asp Pro Lys Arg Leu Gly Pro Leu Arg Gly Phe Gln Trp Val Thr
                100                 105                 110

Gly Asp Asn Asn Thr Ser Tyr Ser Arg Trp Ala Arg Leu Asp Leu Asn
            115                 120                 125

Gly Ala Pro Leu Cys Gly Pro Leu Cys Val Ala Val Ser Ala Ala Glu
        130                 135                 140

Ala Thr Val Pro Ser Glu Pro Ile Trp Glu Glu Gln Gln Cys Glu Val
```

```
              145                 150                 155                 160
Lys Ala Asp Gly Phe Leu Cys Glu Phe His Phe Pro Ala Thr Cys Arg
                  165                 170                 175

Pro Leu Ala Val Glu Pro Gly Ala Ala Ala Ala Val Ser Ile Thr
            180                 185                 190

Tyr Gly Thr Pro Phe Ala Ala Arg Gly Ala Asp Phe Gln Ala Leu Pro
                  195                 200                 205

Val Gly Ser Ser Ala Ala Val Ala Pro Leu Gly Leu Gln Leu Met Cys
        210                 215                 220

Thr Ala Pro Pro Gly Ala Val Gln Gly His Trp Ala Arg Glu Ala Pro
225                 230                 235                 240

Gly Ala Trp Asp Cys Ser Val Glu Asn Gly Gly Cys Glu His Ala Cys
                245                 250                 255

Asn Ala Ile Pro Gly Ala Pro Arg Cys Gln Cys Pro Ala Gly Ala Ala
                260                 265                 270

Leu Gln Ala Asp Gly Arg Ser Cys Thr Ala Ser Ala Thr Gln Ser Cys
            275                 280                 285

Asn Asp Leu Cys Glu His Phe Cys Val Pro Asn Pro Asp Gln Pro Gly
        290                 295                 300

Ser Tyr Ser Cys Met Cys Glu Thr Gly Tyr Arg Leu Ala Ala Asp Gln
305                 310                 315                 320

His Arg Cys Glu Asp Val Asp Asp Cys Ile Leu Glu Pro Ser Pro Cys
                325                 330                 335

Pro Gln Arg Cys Val Asn Thr Gln Gly Gly Phe Glu Cys His Cys Tyr
                340                 345                 350

Pro Asn Tyr Asp Leu Val Asp Gly Glu Cys Val Glu Pro Val Asp Pro
            355                 360                 365

Cys Phe Arg Ala Asn Cys Glu Tyr Gln Cys Gln Pro Leu Asn Gln Thr
        370                 375                 380

Ser Tyr Leu Cys Val Cys Ala Glu Gly Phe Ala Pro Ile Pro His Glu
385                 390                 395                 400

Pro His Arg Cys Gln Met Phe Cys Asn Gln Thr Ala Cys Pro Ala Asp
                405                 410                 415

Cys Asp Pro Asn Thr Gln Ala Ser Cys Glu Cys Pro Glu Gly Tyr Ile
                420                 425                 430

Leu Asp Asp Gly Phe Ile Cys Thr Asp Ile Asp Glu Cys Glu Asn Gly
            435                 440                 445

Gly Phe Cys Ser Gly Val Cys His Asn Leu Pro Gly Thr Phe Glu Cys
        450                 455                 460

Ile Cys Gly Pro Asp Ser Ala Leu Ala Arg His Ile Gly Thr Asp Cys
465                 470                 475                 480

Asp Ser Gly Lys Val Asp Gly Gly Asp Ser Gly Ser Gly Glu Pro Pro
                485                 490                 495

Pro Ser Pro Thr Pro Gly Ser Thr Leu Thr Pro Pro Ala Val Gly Leu
                500                 505                 510

Val His Ser Gly
        515

<210> SEQ ID NO 12
<211> LENGTH: 1548
<212> TYPE: DNA
<213> ORGANISM: human

<400> SEQUENCE: 12
```

-continued

```
atgcttgggg tcctggtcct tggcgcgctg gccctggccg gcctggggtt ccccgcaccc    60
gcagagccgc agccgggtgg cagccagtgc gtcgagcacg actgcttcgc gctctacccg   120
ggccccgcga ccttcctcaa tgccagtcag atctgcgacg gactgcgggg ccacctaatg   180
acagtgcgct cctcggtggc tgccgatgtc atttccttgc tactgaacgg cgacggcggc   240
gttggccgcc ggcgcctctg gatcggcctg cagctgccac ccggctgcgg cgaccccaag   300
cgcctcgggc cctgcgcgg cttccagtgg gttacgggag acaacaacac cagctatagc    360
aggtgggcac ggctcgacct caatgggct cccctctgcg gcccgttgtg cgtcgctgtc    420
tccgctgctg aggccactgt gcccagcgag ccgatctggg aggagcagca gtgcgaagtg   480
aaggccgatg gcttcctctg cgagttccac ttcccagcca cctgcaggcc actggctgtg   540
gagcccggcg ccgcggctgc cgccgtctcg atcacctacg gcaccccgtt cgcggcccgc   600
ggagcggact ccaggcgct gccggtgggc agctccgccg cggtggctcc cctcggctta    660
cagctaatgt gcaccgcgcc gcccggagcg gtccagggc actgggccag ggaggcgccg    720
ggcgcttggg actgcagcgt ggagaacggc ggctgcgagc acgcgtgcaa tgcgatccct   780
ggggctcccc gctgccagtg cccagccggc gccgccctgc aggcagacgg gcgctcctgc   840
accgcatccg cgacgcagtc ctgcaacgac ctctgcgagc acttctgcgt tcccaacccc   900
gaccagccgg gctcctactc gtgcatgtgc gagaccggct accggctggc ggccgaccaa   960
caccggtgcg aggacgtgga tgactgcata ctggagccca gtccgtgtcc gcagcgctgt  1020
gtcaacacac agggtggctt cgagtgccac tgctacccta actacgacct ggtggacggc  1080
gagtgtgtgg agcccgtgga cccgtgcttc agagccaact gcgagtacca gtgccagccc  1140
ctgaaccaaa ctagctacct ctgcgtctgc gccgagggct tcgcgcccat tccccacgag  1200
ccgcacaggt gccagatgtt ttgcaaccag actgcctgtc cagccgactg cgaccccaac  1260
acccaggcta gctgtgagtg ccctgaaggc tacatcctgg acgacggttt catctgcacg  1320
gacatcgacg agtgcgaaaa cggcggcttc tgctccgggg tgtgccacaa cctcccggt   1380 accttcgagt gcatctgcgg gcccgactcg gcccttgccc gccacattgg caccgactgt  1440
gactccggca aggtggacgg tggcgacagc ggctctggcg agcccccgcc cagcccgacg  1500
cccggctcca ccttgactcc tccggccgtg gggctcgtgc attcgggc                1548
```

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
DNA

<400> SEQUENCE: 13

```
aatgtggcgg gcaagggccg a                                               21
```

AGENT FOR PROPHYLACTIC AND/OR THERAPEUTIC TREATMENT OF PERIPHERAL NEUROPATHIC PAIN CAUSED BY ANTICANCER AGENT

TECHNICAL FIELD

The present invention relates to a medicament having a prophylactic and/or therapeutic effect on a peripheral neuropathic pain caused by an anticancer agent.

BACKGROUND ART

In the therapeutic treatment of cancers (malignant tumors), surgery, radiotherapy, and chemotherapy are appropriately used independently or in combination. Anticancer agents (anti-malignant tumor agents) used for cancer chemotherapy among those therapies mentioned above originally have cytotoxicity, and cause side reactions by damaging not only cancer (malignant tumor) cells but also normal cells.

Examples of the side reactions caused by anticancer agents include blood disorders, digestive organ obstructions, and neuropathy, but the, problem of acute or chronic neuropathy is especially becoming more serious in recent years. It is considered that this is because major side reactions caused by emerging anticancer agents having marked anticancer effect are neuropathies in, many cases, development of neuropathy is enhanced by influence of multi-drug therapies such as the FOLFOX™ therapy, and such side reactions as blood disorders and digestive organ obstructions tend to be improved. Under the current circumstances, in order to control such neuropathy caused by anticancer agents, it is obliged to reduce the doses of anticancer agents or discontinue cancer chemotherapies.

Neuropathies caused by anticancer agents are also observed in sensitive organs such as gustatory organs, as well as in the central nervous system, vegetative nervous system, and peripheral nervous system. Among them, peripheral neuropathies, for example, pains such as intense pain and burning pain, numbness of extremity ends, abnormal sensations such as cold hypersensitivity, dysesthesias such as anesthesia and sensory paralysis, sensory ataxia, muscle force reduction, and the like are highly frequently developed, and cold allodynia and mechanical allodynia especially cause problems as typical symptoms. Examples of anticancer agents that frequently cause such peripheral neuropathies include taxane drugs (paclitaxel, docetaxel), vinca alkaloid drugs (vincristine, vinblastine, vindesine, vinorelbine), and platinum preparations (oxaliplatin, cisplatin).

At present, against peripheral neuropathies caused by anticancer agents, especially allodynia, any effective methods for prophylactic and therapeutic treatments have not been established. Although usefulness of intravenous administration of calcium and magnesium or glutathione have been reported for peripheral neuropathies caused by oxaliplatin, it is hardly used because, for example, such therapy further complicates cancer chemotherapy, and such substances require massive administration. In practical clinical fields, it is undesirably required to control peripheral neuropathies caused by anticancer agents with physiotherapy, complementary therapies such as massage and acupuncture, or combination of drug therapies such as those using steroids, antidepressants, antiepileptics, and opioids, however, effectiveness of these therapies has not been verified, and such therapies themselves frequently cause side reactions (Non-patent documents 1 and 2).

Thrombomodulin has been known as a substance that acts to specifically bind to thrombin so as to inhibit the blood coagulation activity of thrombin, and at the same time, exerts anticoagulant activity so as to significantly promote the ability of thrombin to activate Protein C. Thrombomodulin was first discovered and obtained as a glycoprotein expressed on the vascular endothelial cells of various animal species including humans, and as for the structure thereof, it is composed of 5 regions, namely, an N-terminal region (amino acid residues 1 to 226), a region having six EGF-like structures (amino acid residues 227 to 462), an O-linked glycosylation region (amino acid residues 463 to 497), a transmembrane region (amino acid residues 498 to 521), and a cytoplasmic region (amino acid residues 522 to 557), from the N-terminal side of the protein (Non-patent document 3).

The entire length thrombomodulin is hardly dissolved in the absence of a surfactant, and addition of a surfactant is essential for manufacturing an entire thrombomodulin preparation. A soluble thrombomodulin is also available that can be fully dissolved even in the absence of a surfactant. The soluble thrombomodulin may be prepared by removing at least a part of the transmembrane region or the entire transmembrane region. For example, it has been confirmed that a soluble thrombomodulin consisting of only 3 regions, namely, the N-terminal region, the region having six EGF-like structures, and the O-linked glycosylation region (i.e., a soluble thrombomodulin having an amino acid sequence consisting of amino acid residues 19 to 516 of SEQ ID NO: 9) can be obtained by applying recombination techniques, and that the resulting recombinant soluble thrombomodulin has the same activity as that of the natural thrombomodulin (Patent document 1). Thrombomodulins derived from human urine, and the like are also exemplified (Patent document 2).

As recognized in many cases, as a result of spontaneous mutations or mutations occurring at the time of obtainment, polymorphic mutations have been found in the human genes. At present, thrombomodulin proteins in which the amino acid at the position 473 of human thrombomodulin precursor having the amino acid sequence consisting of 575 amino acid residues is converted to Val or Ala have been identified. In the nucleotide sequence encoding the amino acid sequence, this variation of amino acid residue corresponds to mutation to T or C at the position 1418 (Non-patent document 3). However, the two types of thrombomodulins are completely identical in terms of their activity and physicochemical properties, and it can be considered that they are substantially identical.

As for intended uses of thrombomodulin, the substance has so far been expected for uses in therapeutic and prophylactic treatments of diseases, for example, myocardial infarction, thrombosis (for example, cerebral thrombosis of an acute stage or chronic stage, acute or chronic peripheral thrombosis of artery or vein, and the like), embolism (for example, cerebral embolism of an acute stage or chronic stage, acute or chronic peripheral embolism of artery or vein, and the like), peripheral vessel obstructions (for example, Buerger's disease, Raynaud's disease, and the like), obstructive arteriosclerosis, functional obstructions developed in succession to a cardiac operation, complications of organ transplant, disseminated intravascular coagulation (DIC), angina pectoris, transient ischaemic attack, toxemia of pregnancy, deep venous thrombosis (DVT), and the like. Further, examples of applicable diseases, other than those accompanied by hypercoagulation such as thrombosis and DIC, include liver affections (Patent document 4), absorptive bone diseases (Patent document 5), wound healing (Patent document 6), and the like. Furthermore, as uses of thrombomodulin together with other active ingredients, there have been disclosed wound healing (Patent document 7), protection of brain tissues (Patent document 8), and the like. Moreover, use of thrombomodulin for therapeutic and prophylactic treatments of pain with hematopoietic cell transplantation has been disclosed (Patent document 9).

PRIOR ART REFERENCES

Patent Documents

Patent document 1: Japanese Patent Unexamined Publication (KOKAI) No. 64-6219
Patent document 2: Japanese Patent Unexamined Publication No. 3-86900
Patent document 3: WO92/00325
Patent document 4: Japanese Patent Unexamined Publication No. 8-3065
Patent document 5: Japanese Patent Unexamined Publication No. 8-301783
Patent document 6: Japanese Patent Unexamined Publication No. 9-20677
Patent document 7: U.S. Pat. No. 5,976,523
Patent document 8: U.S. Pat. No. 5,827,832
Patent document 9: Japanese Patent Unexamined Publication No. 2012-001543

Non-Patent Documents

Non-patent document 1: NCI Cancer Bulletin, 2010, Feb. 23, 7 (4)
Non-patent document 2: Folia Pharmacologica Japonica (Nippon Yakurigaku Zasshi), 2010, 136:275-279
Non-patent document 3: EMBO Journal, 1987, 6:1891-1897

SUMMARY OF THE INVENTION

Object to be Achieved by the Invention

An object of the present invention is to provide a medicament that enables effective prophylactic and/or therapeutic treatment of a peripheral neuropathic pain caused by anticancer agent(s).

Means for Achieving the Object

The inventors of the present invention strongly recognized the current situations as problems that, for dealing with the neuropathy caused by an anticancer agent, it was forced to reduce the dose of the anticancer agent or to discontinue administration of the anticancer agent, and that any effective prophylactic and therapeutic treatments of neuropathy caused by an anticancer agent had not yet been established, and they considered that it was an important object to provide a medicament for effective prophylactic and/or therapeutic treatment of neuropathy caused by an anticancer agent, especially peripheral neuropathic pain caused by an anticancer agent. This is because the inventors of the present invention considered that peripheral neuropathic pains caused by an anticancer agent made daily living of patients difficult, and constituted the most significant reason for discontinuation of therapeutic treatment of cancer, and therefore solving the problem of allodynia caused by an anticancer agent was important for therapeutic treatment of cancer not only for improving quality of life of patients, but also from a viewpoint of continuation of the therapeutic treatment of cancer.

The inventors of the present invention conducted various researches to achieve the aforementioned object. As a result, they surprisingly found that thrombomodulin exhibited superior prophylactic and/or therapeutic effect against a peripheral neuropathic pain, specifically allodynia, caused by an anticancer agent, and accomplished the present invention. Any prophylactic and/or therapeutic treatment of neuropathy caused by an anticancer agent, especially peripheral neuropathic pain caused by an anticancer agent, with thrombomodulin has not so far been reported or suggested. Although Patent document 9 discloses that thrombomodulin has an effect on pain accompanied by weight increase due to edema, reservoir of ascites, or the like caused by pretreatments of hematopoietic cell transplantation, the document does not mention or suggest peripheral neuropathic pain caused by an anticancer agent at all.

The present invention thus provides the followings.

[1] A medicament for prophylactic and/or therapeutic treatment of a peripheral neuropathic pain caused by an anticancer agent, which comprises thrombomodulin as an active ingredient.
[2] The medicament according to [1] mentioned above, wherein the thrombomodulin is a soluble thrombomodulin.
[3] The medicament according to [1] mentioned above, wherein the thrombomodulin is a human thrombomodulin.
[4] The medicament according to any one of [1] to [3] mentioned above, wherein the peripheral neuropathic pain is one or more kinds of symptoms selected from numbness of extremities, pain of extremities, reduction of deep tendon reflection, reduction of muscle force, allodynia, hyperalgesia, and motor dysfunction.
[5] The medicament according to any one of [1] to [4] mentioned above, wherein the peripheral neuropathic pain is allodynia.
[6] The medicament according to [5] mentioned above, wherein the allodynia is mechanical allodynia.
[6-2] The medicament according to [5] mentioned above, wherein allodynia is cold allodynia.
[7] The medicament according to any one of [1] to [6-2] mentioned above, wherein the anticancer agent consists of one or more kinds of agents selected from the group consisting of a taxane drug and a platinum preparation.
[7-2] The medicament according to [7] mentioned above, wherein the taxane drug consists of one or more kinds of drugs selected from the group consisting of paclitaxel and docetaxel.
[7-3] The medicament according to [7] mentioned above, wherein the platinum preparation consists of one or more kinds of preparations selected from the group consisting of oxaliplatin, cisplatin, carboplatin, and nedaplatin.
[8] The medicament according to any one of [1] to [6-2] mentioned above, wherein the anticancer agent is paclitaxel.
[8-2] The medicament according to any one of [1] to [6-2] mentioned above, wherein the anticancer agent is oxaliplatin.
[9] The medicament according to any one of [1] to [6-2] mentioned above, wherein the anticancer agent is administered according to FOLFOX™ therapy or FOLFIRI therapy.
[10] The medicament according to any one of [1] to [9] mentioned above, wherein thrombomodulin is intermittently administered.

When the cited item numbers are indicated as a range like [1] to [9] as mentioned above, and an item indicated with an item number having a sub-number such as [7-2] is included in the range, it means that the item indicated with the item number having a sub-number such as [7-2] is also cited. This rule also holds for the following descriptions.

[10-2] The medicament according to [10] mentioned above, wherein the intermittent administration is administration of once a week.

[10-3] The medicament according to [10] mentioned above, wherein the intermittent administration is everyday administration.

[10-4] The medicament according to any one of [1] to [9] mentioned above, wherein thrombomodulin is administered once a week.

[10-5] The medicament according to any one of [1] to [9] mentioned above, wherein thrombomodulin is administered every day.

[11] The medicament according to any one of [1] to [10-5] mentioned above, which is administered to a cancer patient suffering from one or more kinds of cancers selected from the group consisting of ovarian cancer, non-small cell cancer, breast cancer, gastric cancer, endometrial cancer, head and neck cancer, esophageal carcinoma, leukemia, malignant lymphoma, pediatric tumor, multiple myeloma, malignant astrocytoma, neuroglioma, trophoblastic disease, germ cell tumor, lung cancer, orchioncus, vesical cancer, renal pelvic tumor, urethrophyma, prostate cancer, uterine cervix carcinoma, neuroblastoma, small cell lung cancer, osteosarcoma, malignant pleural mesothelioma, malignant osteoncus, and colon cancer.

[12] A medicament for administration together with an anticancer agent for prophylactic and/or therapeutic treatment of a peripheral neuropathic pain caused by the anticancer agent, which comprises thrombomodulin as an active ingredient.

[12-2] The medicament according to [12] mentioned above, wherein the anticancer agent is a taxane drug or a platinum preparation.

[12-3] The medicament according to [12] mentioned above, wherein the anticancer agent is paclitaxel.

[12-4] The medicament according to [12] mentioned above, wherein the anticancer agent is oxaliplatin.

[13] The medicament according to any one of [1] to [12-4] mentioned above, wherein the thrombomodulin is a peptide obtainable from a transformed cell prepared by transfecting a host cell with a DNA coding for the amino acid sequence of (i-1) or (i-2) mentioned below, and the peptide is a peptide having the thrombomodulin activities;
(i-1) the amino acid sequence of SEQ ID NO: 9 or 11, or
(i-2) the amino acid sequence of (i-1) mentioned above, further including substitution, deletion or addition of one or more amino acid residues.

[13-2] The medicament according to any one of [1] to [12-4] mentioned above, wherein the thrombomodulin is a peptide obtainable from a transformed cell prepared by transfecting a host cell with a DNA coding for the amino acid sequence of (i-1) mentioned below, and the peptide is a peptide having the thrombomodulin activities;
(i-1) the amino acid sequence of SEQ ID NO: 9 or 11.

[14] The medicament according to any one of [1] to [12-4] mentioned above, wherein the thrombomodulin is a peptide containing the amino acid sequence of (i-1) or (i-2) mentioned below, and the peptide is a peptide having the thrombomodulin activities;
(i-1) the amino acid sequence of the positions 19 to 516 in the amino acid sequence of SEQ ID NO: 9 or 11, or
(i-2) the amino acid sequence of (i-1) mentioned above, further including substitution, deletion or addition of one or more amino acid residues.

[14-2] The medicament according to any one of [1] to [12-4] mentioned above, wherein the thrombomodulin is a peptide containing the amino acid sequence of (i-1) mentioned below, and the peptide is a peptide having the thrombomodulin activities;
(i-1) the amino acid sequence of the positions 19 to 516 in the amino acid sequence of SEQ ID NO: 9 or 11.

[14-3] The medicament according to any one of [1] to [12-4] mentioned above, wherein the thrombomodulin is a peptide containing:
(i) the amino acid sequence of the positions 367 to 480 in the amino acid sequence of SEQ ID NO: 9 or 11, and the amino acid sequence of (ii-1) or (ii-2) mentioned below, and the peptide is a peptide having the thrombomodulin activities:
(ii-1) the amino acid sequence of the positions 19 to 244 in the amino acid sequence of SEQ ID NO: 9 or 11, or
(ii-2) the amino acid sequence of (ii-1) mentioned above, further including substitution, deletion or addition of one or more amino acid residues.

[14-4] The medicament according to any one of [1] to [12-4] mentioned above, wherein the thrombomodulin is a peptide containing:
(i) the amino acid sequence of the positions 367 to 480 in the amino acid sequence of SEQ ID NO: 9 or 11, and the amino acid sequence of (ii-1) mentioned below, and the peptide is a peptide having the thrombomodulin activities:
(ii-1) the amino acid sequence of the positions 19 to 244 in the amino acid sequence of SEQ ID NO: 9 or 11.

[15] A method for prophylactic and/or therapeutic treatment of a peripheral neuropathic pain caused by an anticancer agent, which comprises the step of administering thrombomodulin to a mammal.

[15-2] The method according to [15] mentioned above, which has one or more of the characteristics defined in [1] to [14-4] mentioned above.

[16] Use of thrombomodulin for manufacture of a medicament for prophylactic and/or therapeutic treatment of a peripheral neuropathic pain caused by an anticancer agent.

[16-2] The use according to [16] mentioned above, which has one or more of the characteristics defined in [1] to [14-4] mentioned above.

[17] A method for prophylactic and/or therapeutic treatment of a peripheral neuropathic pain caused by an anticancer agent of a mammal being administered with the anticancer agent, which comprise the step of administering thrombomodulin to the mammal.

[17-2] The method according to [17] mentioned above, which has one or more of the characteristics defined in [1] to [14-4] mentioned above.

[17.3] The method according to [17] mentioned above, which comprises the step of administering thrombomodulin to the mammal simultaneously with the anticancer agent, or at different time.

Effect of the Invention

The present invention enables effective prophylactic and/or therapeutic treatment of a peripheral neuropathic pain caused by an anticancer agent. In order to control peripheral neuropathic pain caused by an anticancer agent, it has so far been undesirably necessary to reduce dose of the anticancer agent, or discontinue cancer chemotherapy. The present invention enables continuation of appropriate cancer chemotherapy, and contribution to improvement of patients' quality of life.

White downward arrow: Administration of 4 mg/kg paclitaxel

Black downward arrow: Administration of TMD123
○: Solvent administration group
●: PTX administration group
△: PTX+0.1 mg/kg TMD123 administration group
Gray △: PTX+1 mg/kg TMD123 administration group
Black △: PTX+10 mg/kg TMD123 administration group
*: $p<0.05$
**: $p<0.01$ (comparison with solvent administration group)
†: $p<0.05$
†††: $p<0.001$ (comparison with PTX administration group)

Figure 1:
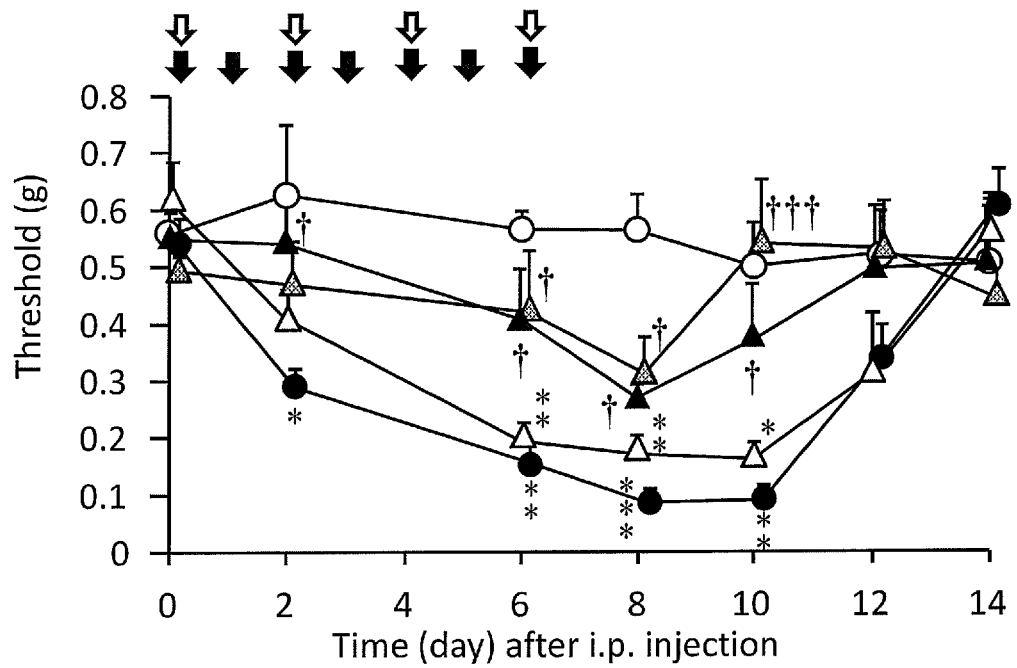
FIG. 1 shows the results of investigation of the prophylactic effect of thrombomodulin on mechanical allodynia caused by paclitaxel administration, which investigation was performed according to the von Frey test.
Figure 2:
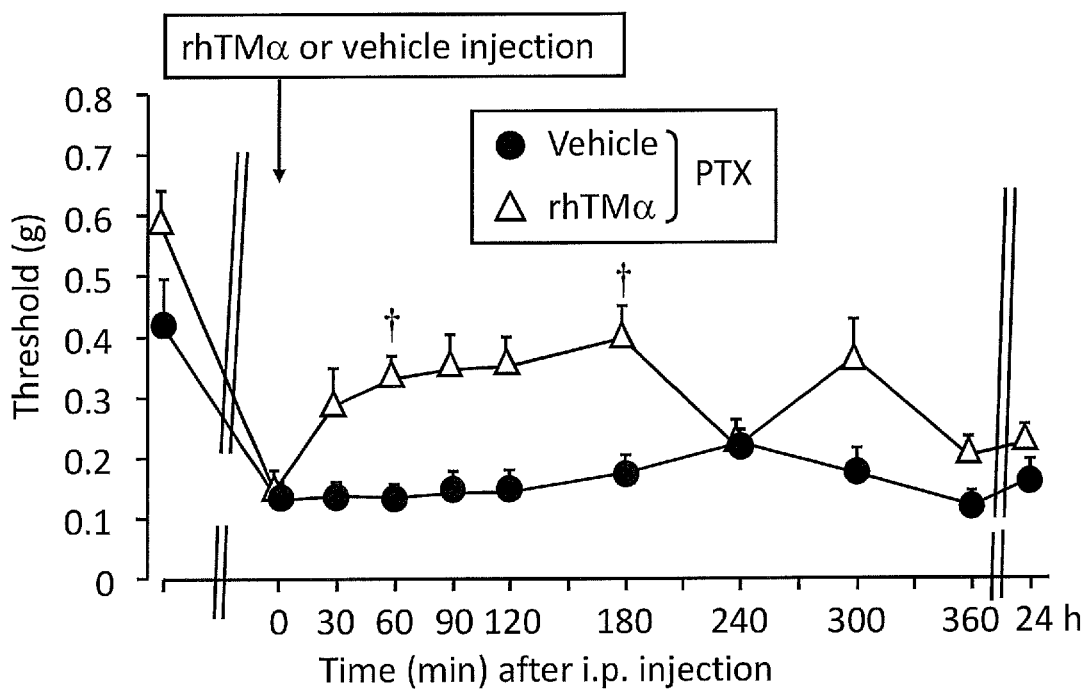

FIG. 2 shows the results of investigation of the therapeutic effect of thrombomodulin on mechanical allodynia caused by paclitaxel administration, which investigation was performed according to the von Frey test, like the investigation of which results are shown in FIG. 1.
●: PTX administration group
△: PTX+10 mg/kg TMD123 administration group
†: $p<0.05$ (comparison with PTX administration group)
rhTMα: TMD123

Figure 3:
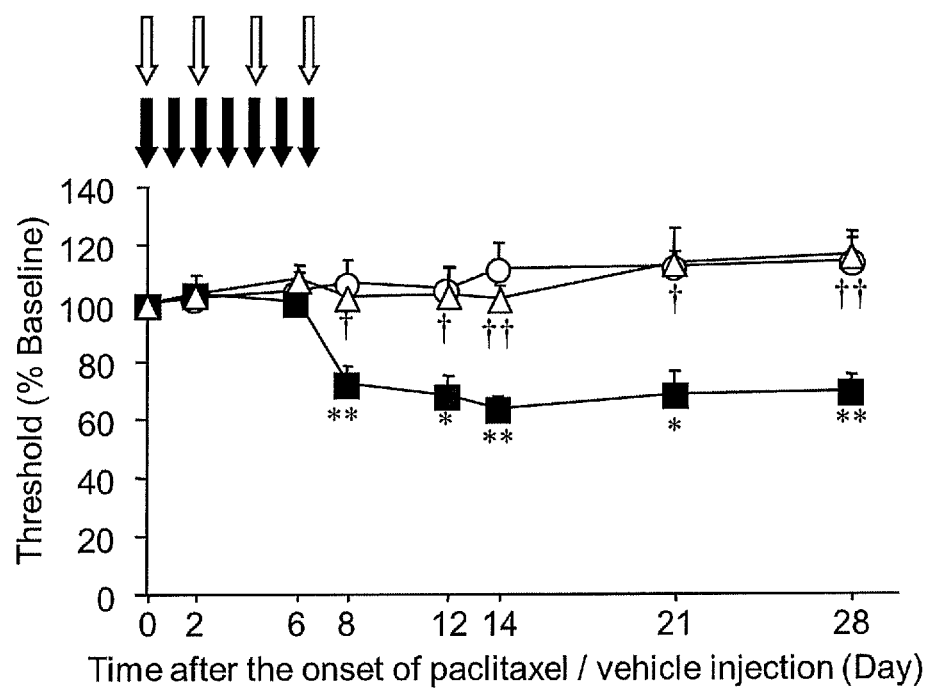

FIG. 3 shows the results of investigation of the therapeutic effect of thrombomodulin on mechanical allodynia caused by paclitaxel administration, which investigation was performed according to the Randall-Selitto test by using rats, like the investigation of which results are shown in FIG. 1.

White downward arrow: Administration of 2 mg/kg paclitaxel

Black downward arrow: Administration of TMD123
◎: Solvent administration group
■: PTX administration group
△: PTX+10 mg/kg TMD123 administration group
*: $p<0.05$
**: $p<0.01$ (comparison with solvent administration group)
†: $p<0.05$
††: $p<0.01$ (comparison with PTX administration group)

MODES FOR CARRYING OUT THE INVENTION

Hereafter, several preferred embodiments of the present invention (preferred modes for carrying out the invention, henceforth also referred to as "embodiments" in the specification) will be specifically explained. However, the scope of the present invention is not limited to the specific embodiments explained below.

Examples of thrombomodulin useful as an active ingredient of the medicament for prophylactic and/or therapeutic treatment of a peripheral neuropathic pain caused by an anticancer agent of this embodiment include soluble thrombomodulin.

The thrombomodulin of this embodiment preferably is known to have an action of (1) selectively binding to thrombin (2) to promote activation of Protein C by thrombin. In addition, it is preferred that the thrombomodulin is confirmed to generally have (3) an action of extending thrombin clotting time, (4) an action of suppressing platelet aggregation caused by thrombin, and/or (5) anti-inflammatory action. Such actions possessed by thrombomodulin may be referred to as thrombomodulin activities.

As the thrombomodulin activities, thrombomodulin preferably has the actions of (1) and (2) mentioned above, and more preferably has the actions of (1) to (4) mentioned above. As the thrombomodulin activities, thrombomodulin more preferably has all of the actions of (1) to (5) mentioned above.

The action of thrombomodulin to bind with thrombin can be confirmed by the study methods described in various known publications such as Thrombosis and Haemostasis, 1993, 70(3):418-422 and The Journal of Biological Chemistry, 1989, 264, 9, pp. 4872-4876. As for the action of promoting activation of Protein C by thrombin, degree of the activity of promoting the activation of Protein C by thrombin or presence or absence of the action can be easily confirmed by the study methods clearly described in various known publications including, for example, Japanese Patent Unexamined Publication No. 64-6219. Further, the action of extending thrombin clotting time, and/or the action of suppressing platelet aggregation caused by thrombin can be similarly and easily confirmed. Furthermore, the anti-inflammatory action can also be confirmed by the study methods described in various known publications including, for example, Blood, 2008, 112:3361-3670 and The Journal of Clinical Investigation, 2005, 115, 5:1267-1274.

The thrombomodulin used for the this embodiment is not particularly limited so far as having the thrombomodulin activities, but the thrombomodulin is preferably a soluble thrombomodulin soluble in water under the condition without surfactants. The solubility of the soluble thrombomodulin in water such as distilled water used for injection (in the absence of a surfactant such as Triton X-100 or polidocanol, and generally around the neutral pH range) is preferably, for example, 1 mg/mL or more or 10 mg/mL or more; preferably 15 mg/mL or more or 17 mg/mL or more; more preferably 20 mg/mL or more, 25 mg/mL or more, or 30 mg/mL or more; particularly preferably 60 mg/mL or more. In some cases, the solubility is, for example, 80 mg/mL or more, or 100 mg/mL or more. For determining whether or not a soluble thrombomodulin is successfully dissolved in water, it is understood that clear appearance of a solution and the absence of apparently observable insoluble substances is served as simple criteria, after the soluble thrombomodulin is dissolved in water and the solution is observed by visual inspection, for example, just under a white light at a position corresponding to an illumination of approximately 1000 luxes. It is also possible to observe the presence or absence of any residue after filtration.

The molecular weight of the thrombomodulin is not limited so far that it has the thrombomodulin activities as described above. The molecular weight is preferably 100,000 or smaller, more preferably 90,000 or smaller, still more preferably 80,000 or smaller, most preferably 70,000 or smaller, and the molecular weight is preferably 50,000 or larger, most preferably 60,000 or larger. The molecular weight of the soluble thrombomodulin can be easily measured by ordinary methods for measuring molecular weight of protein. Measurement by mass spectrometry is preferred, and MALDI-TOF-MS method is more preferred. For obtaining a soluble thrombomodulin having a molecular weight within a desired range, a soluble thrombomodulin, which is obtained by culturing a transformant cell prepared by transfecting a host cell with a DNA encoding the soluble thrombomodulin using a vector, can be subjected to fractionation using column chromatography or the like as described later.

The thrombomodulin used for the present embodiment preferably comprises the amino acid sequence consisting of the amino acid residues at the positions 19 to 132 of SEQ ID NO: 1, which has been known as the central portion of the thrombomodulin activities of human thrombomodulin, and the thrombomodulin is not particularly limited, so long as the thrombomodulin comprises the amino acid sequence consisting of the amino acid residues at the positions 19 to 132 of SEQ ID NO: 1. The amino acid sequence consisting of the amino acid residues at the positions 19 to 132 of SEQ ID NO: 1 may be naturally or artificially mutated, so long as the sequence has an action to promote the activation of Protein C by thrombin, namely, one of the thrombomodulin activities. Specifically, the sequence may comprise substitution, deletion, or addition of one or more amino acid residues in the amino acid sequence consisting of the amino acid residues at the positions 19 to 132 of SEQ ID NO: 1. Acceptable level of the mutation is not particularly limited, so long as the amino acid sequence has the thrombomodulin activities. An example includes a homology 50% or more as amino acid sequences, and the homology is preferably 70% or more, more preferably 80% or more, further preferably 90% or more, particularly preferably 95% or more, and most preferably 98% or more. Such mutated amino acid sequence including substitution, deletion or addition of one or more amino acid residues is referred to as homologous mutation sequence. As described later, these mutated amino acid sequences can be easily produced by using ordinary gene manipulation techniques. The thrombomodulin is not particularly limited so far that it has the aforementioned sequence and the action of selectively binding to thrombin to promote activation of Protein C by thrombin at least as the whole thrombomodulin, but the thrombomodulin preferably also has the anti-inflammatory action.

The amino acid sequence of SEQ ID NO: 3 comprises the mutation of Val as the amino acid at the position 125 of the sequence of SEQ ID NO: 1 to Ala. The thrombomodulin used for the present invention also preferably comprises the amino acid sequence from the position 19 to 132 of SEQ ID NO: 3.

As described above, although the thrombomodulin used for the present invention is not particularly limited so long that the thrombomodulin has at least the amino acid sequence from the position 19 to 132 of SEQ ID NO: 1 or 3, or a homologous mutation sequence thereof, and comprises at least a peptide sequence having the thrombomodulin activities, preferred examples of the thrombomodulin include a peptide consisting of the sequence from the position 19 to 132 or 17 to 132 in either of SEQ ID NO: 1 or SEQ ID NO: 3, and a peptide consisting of a homologous mutation sequence of the aforementioned sequence and having at least the thrombomodulin activities. A peptide consisting of the sequence from the position 19 to 132 in either of SEQ ID NO: 1 or SEQ ID NO: 3 is more preferred. In another embodiment, a peptide consisting of a homologous mutation sequence of the sequence from the position 19 to 132 or 17 to 132 in either of SEQ ID NO: 1 or SEQ ID NO: 3 and having at least the thrombomodulin activities is more preferred.

As another embodiment of the thrombomodulin used in this embodiment, the thrombomodulin preferably comprises the amino acid sequence from the positions 19 to 480 of SEQ ID NO: 5, which is not particularly limited so long as the thrombomodulin comprises the amino acid sequence from the position 19 to 480 of SEQ ID NO: 5. The amino acid sequence from the positions 19 to 480 of SEQ ID NO: 5 may be a homologous mutation sequence thereof, so long as the sequence has an action to promote the activation of Protein C by thrombin, i.e., one of the thrombomodulin activities.

The sequence of SEQ ID NO: 7 comprises the mutation of Val as the amino acid at the position 473 of the sequence of SEQ ID NO: 5 to Ala. The thrombomodulin used in this embodiment also preferably comprises the amino acid sequence from the position 19 to 480 of SEQ ID NO: 7.

As described above, although the thrombomodulin used in this embodiment is not particularly limited so long as the thrombomodulin has at least the sequence from the position 19 to 480 in either of SEQ ID NO: 5 or SEQ ID NO: 7, or a homologous mutation sequence thereof, and comprises at least a peptide sequence having the thrombomodulin activities, preferred examples of the thrombomodulin include a peptide consisting of the sequence from the position 19 to 480 or 17 to 480 in either of SEQ ID NO: 5 or SEQ ID NO: 7, and a peptide consisting of a homologous mutation sequence of the aforementioned sequence and having at least the thrombomodulin activities. A peptide consisting of the sequence from the position 19 to 480 of SEQ ID NO: 5 or 7 is more preferred. In another embodiment, a peptide consisting of a homologous mutation sequence of the sequence from the position 19 to 480 or 17 to 480 in either of SEQ ID NO: 5 or SEQ ID NO: 7, and having at least the thrombomodulin activities is more preferred.

As another embodiment of the thrombomodulin used in this embodiment, the thrombomodulin preferably comprises the amino acid sequence from the position 19 to 515 of SEQ ID NO: 9, which is not particularly limited so long as the thrombomodulin comprises the amino acid sequence from the position 19 to 515 of SEQ ID NO: 9. The amino acid sequence from the position 19 to 515 of SEQ ID NO: 9 may be a homologous mutation sequence thereof, so long as the sequence has an action to promote the activation of Protein C by thrombin, i.e., one of the thrombomodulin activities.

The amino acid sequence of SEQ ID NO: 11 comprises the mutation of Val as the amino acid at the position 473 of SEQ ID NO: 9 to Ala. The thrombomodulin used in this embodiment also preferably comprises the amino acid sequence from the position 19 to 515 of SEQ ID NO: 11.

As described above, although the thrombomodulin used in this embodiment is not particularly limited so long as the thrombomodulin has at least the sequence from the position 19 to 515 in either of SEQ ID NO: 9 or SEQ ID NO: 11, or a homologous mutation sequence thereof, and comprises a peptide sequence having at least the thrombomodulin activities, more preferred examples include a peptide having the sequence from position 19 to 516, 19 to 515, 17 to 516, or 17 to 515 in either of SEQ ID NO: 9 or SEQ ID NO: 11, and a peptide consisting of a homologous mutation sequence of the aforementioned sequence and having at least the thrombomodulin activities. A peptide having the sequence from the position 19 to 516, 19 to 515, 17 to 516, or 17 to 515 of SEQ ID NO: 9 is particularly preferred. A mixture thereof is also a preferred example. In another embodiment, a peptide having the sequence from the position 19 to 516, 19 to 515, 17 to 516, or 17 to 515 of SEQ ID NO: 11 is particularly preferred. A mixture thereof is also a preferred example. Further, a peptide consisting of a homologous mutation sequence thereof and having at least the thrombomodulin activities is also a preferred example. It is preferred that the soluble thrombomodulin also has the anti-inflammatory action.

A peptide having a homologous mutation sequence is as described above, and means a peptide that may comprise substitution, deletion, or addition of at least one, namely, one or more, preferably several (for example, 1 to 20, preferably 1 to 10, more preferably 1 to 5, particularly preferably 1 to 3) amino acid residues, in the amino acid sequence of the subjected peptide. Although acceptable level of mutation is not particularly limited so long as the peptide has the thrombomodulin activities, an example of the acceptable level of homology includes 50% or more as an amino acid sequences, and the homology may be preferably 70% or more, more preferably 80% or more, further preferably 90% or more, particularly preferably 95% or more, and most preferably 98% or more.

Preferred examples of the thrombomodulin used in this embodiment also include the peptide consisting of the sequence of SEQ ID NO: 14 (462 amino acid residues), the peptide consisting of the sequence of SEQ ID NO: 8 (272 amino acid residues), and the peptide consisting of the sequence of SEQ ID NO: 6 (236 amino acid residues) described in Japanese Patent Unexamined Publication No. 64-6219.

The thrombomodulin used in this embodiment is not particularly limited so long as the thrombomodulin has at least the amino acid sequence from the position 19 to 132 in either of SEQ ID NO: 1 or SEQ ID NO: 3. As such a thrombomodulin, a peptide having at least the amino acid sequence from the position 19 to 480 in either of SEQ ID NO: 5 or SEQ ID NO: 7 is preferred, and a peptide having at least the amino acid sequence from the position 19 to 515 in either of SEQ ID NO: 9 or SEQ ID NO: 11 is more preferred. A more preferred example of the peptide having at least the amino acid sequence from the position 19 to 515 in either of SEQ ID NO: 9 or SEQ ID NO: 11 is a peptide having the sequence from the position 19 to 516, 19 to 515, 19 to 514, 17 to 516, 17 to 515, or 19 to 514 in either of SEQ ID NO: 9 or SEQ ID NO: 11. Furthermore, a mixture of peptides each consisting of the sequence from the position 19 to 516, 19 to 515, 19 to 514, 17 to 516, 17 to 515, or 19 to 514 in either of SEQ ID NO: 9 or SEQ ID NO: 11 is also a preferred example.

In the case of the aforementioned mixture, the mixing ratio of a peptide that starts from the position 17 and a peptide that starts from the position 19 for each of SEQ ID NOS: 9 and 11 is, for example, 30:70 to 50:50, preferably 35:65 to 4555.

Further, the mixing ratio of a peptide that terminates at the position 514, a peptide that terminates at the position 515, and a peptide that terminates at the position 516 for each of SEQ ID NOS: 9 and 11 is, for example, 0:0:100 to 0:90:10, or 0:70:30 to 10:90:0, or 10:0:90 to 20:10:70, if desired.

The mixing ratio of the peptides can be determined by an ordinary method.

The sequence of the positions 19 to 132 in SEQ ID NO: 1 corresponds to the sequence of the positions 367 to 480 in SEQ ID NO: 9, and the sequence of the positions 19 to 480 in SEQ ID NO: 5 corresponds to the sequence of the positions 19 to 480 in SEQ ID NO: 9. Further, the sequence of the positions 19 to 132 in SEQ ID NO: 3 corresponds to the sequence of the positions 367 to 480 in SEQ ID NO: 11, and the sequence of the positions 19 to 480 in SEQ ID NO: 7 corresponds to the sequence of the positions 19 to 480 in SEQ ID NO: 11. Furthermore, all the sequences of the positions 1 to 18 in SEQ ID NOS: 1, 3, 5, 7, 9 and 11 are identical sequences.

As described below, these thrombomodulins used in this embodiment can be obtained from transformant cells prepared by transfecting host cells with a DNA encoding the peptide (specifically, the nucleotide sequences of SEQ ID NOS: 2, 4, 6, 8, 10, 12, and the like) by using a vector.

It is sufficient that these peptides only have the aforementioned amino acid sequences, and a sugar chain may be attached or not attached, which not particularly limited. In gene manipulation techniques, a type of a sugar chain, a position to which a sugar chain is added, and a level of addition thereof differ depending on a type of host cells used, and any techniques may be used. As for binding position of a sugar chain and a type thereof, facts described in Japanese Patent Unexamined Publication No. 11-341990 are known, and the thrombomodulins used in this embodiment may be added with the same sugar chain at the same position. Two types of N-linked sugar chains, those of fucosyl biantennary type and fucosyl triantennary type, may bind to the thrombomodulin of this embodiment, and ratio thereof is, for example, 100:0 to 60:40, preferably 95:5 to 60:40, more preferably 90:10 to 70:30. The ratio of these sugar chains can be measured on a two-dimensional sugar chain map described in Biochemical Experimental Methods, Vol. 23, Methods of Researches on Glycoprotein Sugar Chains, Japan Scientific Societies Press (1990), and the like. Furthermore, when a sugar composition of the thrombomodulin of this embodiment is examined, neutral saccharides, aminosaccharides, and sialic acid are detected, of which content may be, each independently for example, 1 to 30%, preferably 2 to 20%, more preferably 5 to 10%, in terms of weight ratio based on the protein content. The sugar contents can be measured by the methods described in Lecture of New Biochemical Experiments, Vol. 3, Sugar I, Glycoprotein (Book 1), Tokyo Kagaku Dojin (1990) (neutral saccharides: phenol-sulfuric acid method, aminosaccharides: Elson-Morgan method, sialic acid: periodic acid-resorcinol method).

Although the method for obtaining thrombomodulin is not limited to obtaining it by genetic manipulation as described later, as a signal sequence that can be used for expression where the thrombomodulin is obtained by gene manipulation, a nucleotide sequence encoding the amino acid sequence of the positions 1 to 18 in SEQ ID NO: 9, and a nucleotide sequence encoding the amino acid sequence of the positions 1 to 16 in SEQ ID NO: 9 can be used, and other known signal sequences such as the signal sequence of human tissue plasminogen activator can also be used (International Publication WO88/9811).

When a DNA sequence encoding thrombomodulin is introduced into a host cell, examples of preferred methods include a method of incorporating a DNA sequence encoding thrombomodulin into, preferably, a vector, more preferably an expression vector capable of being expressed in animal cells, and then introducing the DNA with the vector. An expression vector is a DNA molecule that is constituted with a promoter sequence, a sequence for adding a ribosome binding site to mRNA, a DNA sequence encoding a protein to be expressed, a splicing signal, a terminator sequence for transcription termination, a replication origin sequence, and the like. Examples of preferred animal cell expression vector include pSV2-X reported by Mulligan R. C. et al. (Proc. Natl. Acad. Sci. U.S.A., 1981, 78, 2072-2076); pBP69T (69-6) reported by Howley P. M. et al. (Methods in Emzymology, 1983, 101, 387-402, Academic Press), and the like. Further, there is also another preferred embodiment in which DNA is introduced into an expression vector expressible in a microorganism.

Examples of host cell that can be used in production of such peptides as mentioned above include animal cells. Examples of the animal cells include Chinese hamster ovary (CHO) cells, COS-1 cells, COS-7 cells, VERO (ATCC CCL-81) cells, BHK cells, canine kidney-derived MDCK cells, hamster AV-12-664 cells, and the like. In addition, examples of host cell derived from human include HeLa cells, WI38 cells, human 293 cells, and PER.C6 cells. Of these cells, CHO cells are very common and preferred, and among the CHO cells, dihydrofolate reductase (DHFR)-deficient CHO cells are more preferred.

In a gene manipulation process or a peptide production process, microorganisms such as *Escherichia coli* are also often used. A host-vector system suitable for each process is preferably used, and an appropriate vector system can also be selected for the aforementioned host cells. A thrombomodulin gene used in a genetic recombination technique has been cloned. Examples of production of thrombomodulin by such a gene recombination technique have been disclosed, and further, methods for purifying thrombomodulin to obtain a purified product thereof are also known (Japanese Patent Unexamined Publication Nos. 64-6219, 2-255699, 5-213998, 5-310787, 7-155176; and J. Biol. Chem., 1989, 264:10351-10353). Therefore, the thrombomodulin used in this embodiment can be produced by using the methods described in the aforementioned reports, or by similar methods. For example, Japanese Patent Unexamined Publication No. 64-6219 discloses the *Escherichia coli* K-12 strain DH5 (ATCC Accession No. 67283) containing a plasmid pSV2TMJ2 that contains a DNA encoding the full-length thrombomodulin. This strain re-deposited at the former National Institute of Bioscience and Human-Technology (currently Independent Administrative Institution, National Institute of Advanced Industrial Science and Technology, International Patent Organism Depositary) (*Escherichia coli* DH5/pSV2TMJ2) (FERM BP-5570) can also be used. The thrombomodulin used in this embodiment can be prepared by a known gene manipulation technique using a DNA encoding the full-length thrombomodulin as a starting material.

The thrombomodulin of this embodiment may be prepared by a conventionally known method or a similar method. For example, the aforementioned method of Yamamoto et al. (Japanese Patent Unexamined Publication No. 64-6219) or the method described in Japanese Patent Unexamined Publication No. 5-213998 can be referred to. Specifically, for example, a DNA encoding the amino acid sequence of SEQ ID NO: 9 is prepared from a human-derived thrombomodulin gene by a gene manipulation technique, and may be further modified as required. For such modification, in order to obtain a DNA encoding the amino acid sequence of SEQ ID NO: 11 (which specifically consists of the nucleotide sequence of SEQ ID NO: 12), codons encoding the amino acid at the position 473 in the amino acid sequence of SEQ ID NO: 9 (in particular, the nucleotide at the position 1418 in SEQ ID NO: 10) are mutated by site-directed mutagenesis according to the method described by Zoller M. J. et al. (Method in Enzymology, 1983, 100:468-500, Academic Press). For example, by using a synthetic DNA for mutation having the nucleotide sequence of SEQ ID NO: 13, the nucleotide T at the position 1418 in SEQ ID NO: 10 may be converted to the nucleotide C to obtain a mutated DNA.

The DNA prepared as described above is incorporated into, for example, Chinese hamster ovary (CHO) cells to obtain transformant cells. Such cells are subjected to appropriate selection, and thrombomodulin purified by a known method can be produced from a culture solution obtained by culturing a selected cell. As described above, the DNA (SEQ ID NO: 10) encoding the amino acid sequence of SEQ ID NO: 9 is preferably transfected into the aforementioned host cell.

The method for producing thrombomodulin of this embodiment is not limited to the aforementioned method. For example, it is also possible to extract and purify the thrombomodulin from urine, blood, other body fluids and the like, or extract and purify the thrombomodulin from a tissue producing thrombomodulin or a culture of the aforementioned tissue and the like. Further, the thrombomodulin may be further subjected to a cleavage treatment using a protease, as required.

For the culture of the aforementioned transformant cell, a medium used for ordinary cell culture may be used, and it is preferable to culture the transformant cell in various kinds of media in advance to choose an optimal medium. For example, a known medium such as MEM medium, DMEM medium, and 199 medium may be used as a base medium, and a further improved medium or a medium added with supplements for various media may be used. Examples of the culture method include serum culture, in which culture is performed in a medium containing blood serum, and serum-free culture, in which culture is performed in a medium not containing blood serum. Although the culture method is not particularly limited, the serum-free culture is preferred.

When serum is added to a medium in the case of the serum culture, bovine serum is preferred. Examples of bovine serum include fetal bovine serum, neonate bovine serum, calf bovine serum, adult bovine serum, and the like, and any of these examples may be used so far that the serum is suitable for the cell culture. As the serum-free medium used in the serum-free culture, commercially available media can be used. Serum-free media suitable for various cells are marketed, and for example, for the CHO cell, CD-CHO, CHO-S-SFMII and CHO-III-PFM are sold by Invitrogen, and IS CHO, IS CHO-CD medium, and the like are sold by Irvine Scientific. These media may be used without any treatment, or they may be improved or added with supplements and used. Examples of the serum-free medium further include the DMEM medium containing 5 mg/L each of insulin, transferrin, and selenious acid. As described above, the medium is not particularly limited so far that the medium can be used to produce the thrombomodulin of this embodiment. The culture method is not particularly limited, and any of batch culture, repetitive batch culture, fed-batch culture, perfusion culture, and the like may be used.

When the thrombomodulin used in this embodiment is prepared by the aforementioned cell culture method, diversity may be observed in the N-terminus amino acid due to posttranslational modification of the protein. For example, the amino acid of the position 17, 18, 19 or 22 in SEQ ID NO: 9 may serve as the N-terminus amino acid. Further, for example, the N-terminus amino acid may be modified so that the glutamic acid at the position 22 is changed to pyroglutamic acid. It is preferred that the amino acid of the position 17 or 19 serves as the N-terminus amino acid, and it is more preferred that the amino acid of the position 19 serves as the N-terminus amino acid. Further, there is also another embodiment in which the amino acid of the position 17 serves as the N-terminus amino acid, which is a preferred embodiment. As for the modification, diversity and the like mentioned above, similar examples can be mentioned for the sequence of SEQ ID NO: 11.

Further, when the soluble thrombomodulin is prepared by using a DNA having the nucleotide sequence of SEQ ID NO: 10, diversity of the C-terminus amino acid may be observed, and a peptide shorter by one amino acid residue may be produced. Specifically, the C-terminus amino acid may be modified so that the amino acid of the position 515 serves as the C-terminus amino acid, and further the position 515 is amidated. Further, a peptide shorter by two amino acid residues may be produced. Specifically, the amino acid of the position 514 may serve as the C-terminus amino acid.

Therefore, any of peptides having significant diversity of the N-terminus amino acid and C-terminus amino acid, or a mixture of them may be produced. It is preferred that the amino acid of the position 515 or the amino acid of the position 516 serves as the C-terminus amino acid, and it is more preferred that the amino acid of the position 516 serves as the C-terminus amino acid. Further, there is also another embodiment in which the amino acid of the position 514 serves as the C-terminus amino acid, which is a preferred embodiment. Concerning the modification, diversity and the like described above, the same shall apply to a DNA having the nucleotide sequence of SEQ ID NO: 12.

The thrombomodulin obtained by the method described above may be a mixture of peptides having diversity in the N-terminus and C-terminus amino acids. Specific examples include a mixture of peptides having the sequences of the positions 19 to 516, positions 19 to 515, positions 19 to 514, positions 17 to 516, positions 17 to 515, and positions 17 to 514 in SEQ ID NO 9.

Then, isolation and purification of thrombomodulin from a culture supernatant or culture obtained as described above can be carried out by known methods [edited by Takeichi Horio, *Tanpakushitsu/Koso no Kiso Jikken Ho* (Fundamental Experimental Methods for Proteins and Enzymes), 1981]. For example, it is preferable to use ion exchange chromatography or adsorption chromatography, which utilizes an interaction between thrombomodulin and a chromatographic carrier on which functional groups having a charge opposite to that of thrombomodulin are immobilized. Another preferred example is affinity chromatography utilizing specific affinity with thrombomodulin. Preferred examples of adsorbent include thrombin that is a ligand of thrombomodulin and an anti-thrombomodulin antibody. As the antibody, anti-thrombomodulin antibodies having appropriate properties or recognizing appropriate epitopes can be used. Examples include, for example, those described in Japanese Patent Publication (Kokoku) No. 5-42920, Japanese Patent Unexamined Publication Nos. 64-45398 and 6-205692 and the like. Other examples include gel filtration chromatography and ultrafiltration, which utilize the molecular size of thrombomodulin. Other examples further include hydrophobic chromatography that utilizes hydrophobic bond between a chromatographic carrier on which hydrophobic groups are immobilized, and a hydrophobic portion of thrombomodulin. Furthermore, hydroxyapatite may be used as a carrier in adsorption chromatography, of which examples include, for example, those described in Japanese Patent Unexamined Publication No. 9-110900. These means may be used in combination, as required. Although degree of purification can be selected depending on a purpose of use and the like, it is desirable to purify thrombomodulin until a single band is obtained as a result of electrophoresis, preferably SDS-PAGE, or a single peak is obtained as a result of gel filtration HPLC or reverse phase HPLC of the isolated and purified product. It should of course be understood that, when two or more types of thrombomodulins are used, it is preferred that only the bands of the thrombomodulins are substantially obtained, and it is not required to obtain one single band.

Specific examples of the purification method used in this embodiment include a purification method using the thrombomodulin activities as a criterion, for example, a purification method comprising roughly purifying a culture supernatant or a culture product with an ion exchange column Q-Sepharose Fast Flow to collect a fraction having the thrombomodulin activities; then purifying the fraction with an affinity column, DIP-thrombin-agarose (diisopropylphosphorylthrombin agarose) column, as the main purification step to recover a fraction having potent thrombomodulin activities; then concentrating the recovered fraction and followed by gel filtration to obtain a thrombomodulin active fraction as a purified product (Gomi K. et al., Blood, 1990, 75: 1396-1399). An example of the thrombomodulin activities used as the criterion is an activity of promoting the activation of Protein C by thrombin. Other preferred examples of the purification method will be exemplified below.

An appropriate ion exchange resin having good adsorptive condition for thrombomodulin is selected, and purification by ion exchange chromatography is performed. A particularly preferred example is a method comprising the use of Q-Sepharose Fast Flow equilibrated with a 0.02 mol/L Tris-HCl buffer (pH 7.4) containing 0.18 mol/L NaCl. After washing as required, elution can be performed with a 0.02 mol/L Tris-HCl buffer (pH 7.4) containing 0.3 mol/L NaCl, for example, to obtain thrombomodulin as a roughly purified product.

Then, for example, a substance having specific affinity for thrombomodulin can be immobilized on a resin to perform affinity chromatography purification. Preferred examples include a DIP-thrombin-agarose column and an anti-thrombomodulin monoclonal antibody column. In the case of the DIP-thrombin-agarose column, the column is equilibrated beforehand with a 20 mmol/L Tris-HCl buffer (pH 7.4) containing 100 mmol/L NaCl and 0.5 mmol/L calcium chloride, and the aforementioned roughly purified product can be then charged on the column, washed as required, and then eluted with, for example, a 20 mmol/L Tris-HCl buffer (pH 7.4) containing 1.0 mol/L NaCl and 0.5 mmol/L calcium chloride to obtain thrombomodulin as a purified product. In the case of the anti-thrombomodulin monoclonal antibody column, an example of the method comprises: contacting an anti-thrombomodulin monoclonal antibody solution in a 0.1 mol/L NaHCO$_3$ buffer (pH 8.3) containing 0.5 mol/L NaCl with Sepharose 4FF (GE Health Care Biosciences) activated with CNBr beforehand to obtain the resin Sepharose 4FF coupled with the anti-thrombomodulin monoclonal antibodies, equilibrating the resin filled in a column beforehand with, for example, a 20 mmol/L phosphate buffer (pH 7.3) containing 0.3 mol/L NaCl, washing the resin as required, and then performing elution with a 100 mmol/L glycine-HCl buffer (pH 3.0) containing 0.3 mol/L NaCl. An effluent may be neutralized with an appropriate buffer to obtain a product as a purified product.

Subsequently, the purified product is adjusted to pH 3.5, and then charged on a cation exchanger, preferably SP-Sepharose FF (GE Health Care Biosciences) as a strong cation exchanger, equilibrated with a 100 mmol/L glycine-HCl buffer (pH 3.5) containing 0.3 mol/L NaCl, and washing is performed with the same buffer to obtain a non-adsorptive fraction. The resulting fraction is neutralized with an appropriate buffer to obtain a highly purified product. These products are preferably concentrated by ultrafiltration.

Further, it is also preferable to exchange the buffer by gel filtration. For example, a highly purified product concentrated by ultrafiltration can be charged on a Sephacryl S-300 column or S-200 column equilibrated with a 20 mmol/L phosphate buffer (pH 7.3) containing 50 mmol/L NaCl, and then developed for fractionation with a 20 mmol/L phosphate buffer (pH 7.3) containing 50 mmol/L NaCl. The activity for promoting the activation of Protein C by thrombin can be confirmed to collect an active fraction and thereby obtain a buffer-exchanged highly purified product. In order to improve safety, a highly purified product obtained as described above is preferably filtered through an appropriate filter for eliminating viruses such as Planova 15N (Asahi Kasei Medical Co., Ltd.), and then the resultant can be concentrated by ultrafiltration to a desired concentration. Finally, the product is preferably filtered through an aseptic filtration filter.

The "cancer chemotherapy" referred to in this embodiment means a method of treating a cancer using an anticancer agent.

The "anticancer agent" referred to in this embodiment is not particularly limited so long as it is a medicament having an anticancer activity, which causes symptoms of peripheral neuropathic pain as side reactions when it is administered to a patient. Examples include, for example, anticancer agents that inhibit metabolism of nucleic acids (platinum preparation and the like), anticancer agents that inhibit microtubule polymerization (vinca alkaloid agents), anticancer agents that inhibit microtubule depolymerization (taxane agents), anticancer agents showing hormone antagonistic action (anti-estrogen agents and the like), anticancer agents that inhibit intracellular signal transduction (proteosome inhibitors and the like), anticancer agents that act on a molecular target specific to a malignant tumor (tyrosine kinase inhibitors, antibody preparations, and the like), and anticancer agents showing a nonspecific immunity activation action (hemolytic *streptococcus* preparations and the like), and anticancer agents that inhibit metabolism of nucleic acids, and anticancer agents that inhibit microtubule polymerization or depolymerization are preferred. For example, the anticancer agent includes one or more kinds of anticancer agents selected from the group consisting of taxane agents and platinum preparations, and preferred is a taxane agent or a platinum preparation, and a taxane agent is more preferred. In another embodiment, a platinum preparation may be preferred.

Examples of the taxane agents include paclitaxel, docetaxel, tamoxifen, and the like. One or more kinds selected from the group consisting of paclitaxel and docetaxel are preferred, and paclitaxel is more preferred.

Examples of the platinum preparations include oxaliplatin, cisplatin, carboplatin, nedaplatin, and the like. One or more kinds of preparations selected from the group consisting of oxaliplatin, cisplatin, carboplatin, and nedaplatin are preferred, and oxaliplatin is more preferred.

The peripheral neuropathic pain caused by an anticancer agent, which is the

The peripheral neuropathic pain caused by an anticancer agent, which is the object of the prophylactic and/or therapeutic treatment using the medicament of this embodiment, include at least a peripheral neuropathic pain caused by a single drug therapy using a single kind of anticancer agent, and also encompasses a peripheral neuropathic pain caused by a multi-drug therapy using two or more kinds of medicaments in combination based on different modes of actions. Examples of the multi-drug therapy include, for example, the FOLFOX™ therapy, FOLFIRI therapy, and the like, but the therapy is not limited to these examples. As the object of application of the medicament of this embodiment, for example, a peripheral neuropathic pain caused by the FOLFOX™ therapy is preferred. In another embodiment, a peripheral neuropathic pain caused by the FOLFIRI therapy may be preferred.

The FOLFOX™ therapy is one class of cancer chemotherapy that uses oxaliplatin, fluorouracil, and levofolinate in combination. The FOLFOX™ therapy is classified into, for example, FOLFOX™2, FOLFOX™3, FOLFOX™4, FOLFOX™6, mFOLFOX™6, FOLFOX™7, mFOLFOX™7, and the like according to the administration method.

The FOLFIRI therapy is one class of the cancer chemotherapy that uses irinotecan, fluorouracil, levofolinate, and leucovorin in combination.

The FOLFOX therapy is one class of cancer chemotherapy that uses oxaliplatin, fluorouracil, and levofolinate in combination. The FOLFOX therapy is classified into, for example, FOLFOX2, FOLFOX3, FOLFOX4, FOLFOX6, mFOLFOX6, FOLFOX7, mFOLFOX7, and the like according to the administration method.

The FOLFIRI therapy is one class of the cancer chemotherapy that uses irinotecan, fluorouracil, and levofolinate in combination.

Examples of the anticancer agents that inhibit metabolism of nucleic acids include, for example, alkylating agents (for example, cyclophosphamide and nimustine), antitumor antibiotics (for example, doxorubicin, mitomycin C, and bleomycin), topoisomerase inhibitors (for example, irinotecan, and ethoposide), platinum preparations (for example, cisplatin, carboplatin and oxaliplatin), pyrimidine metabolism inhibitors (for example, mercaptopurine, and fludarabine), and folic acid synthesis inhibitors (for example, methotrexate). Among them, platinum preparations are preferred, and oxaliplatin is more preferred, since it is an anticancer agent that most frequently causes peripheral neuropathic pain, and a method for treating such peripheral neuropathic pain is strongly desired.

Examples of the anticancer agents that inhibit microtubule polymerization or depolymerization include vinca alkaloid agents (for example, vincristine, and vinblastine), taxane agents (for example, paclitaxel, docetaxel, and tamoxifen), and anti-androgen agents (for example, flutamide). Among them, taxane agents are preferred, and paclitaxel is more preferred.

Examples of the anticancer agents having hormone antagonistic action include, for example, anti-estrogen agents (for example, tamoxifen), and anti-androgen agents (for example, flutamide).

Examples of the anticancer agents that inhibit intracellular signal transduction include, for example, proteosome inhibitors (for example, bortezomib).

Examples of the anticancer agents that act on a molecular target specific to a malignant tumor include, for example, BCR/ABL tyrosine kinase inhibitors (for example, imatinib), EGFR tyrosine kinase inhibitors (for example, gefitinib), antibody preparations (for example, rituximab, trastuzumab, and tocilizumab), and arsenic preparations.

Examples of the anticancer agents having a nonspecific immunity activation action include, for example, hemolytic *streptococcus* preparations and *Coriolus* polysaccharide preparations.

The "peripheral neuropathic pain caused by an anticancer agent" referred to in this embodiment means a peripheral neuropathic pain caused as a result of administration of such an anticancer agent as exemplified above. It may also be referred to as "chemotherapy-induced peripheral neuropathic pain". Examples of the symptoms of peripheral neuropathic pain include numbness of extremities, pain of extremities, reduction of deep tendon reflection, reduction of muscle force, allodynia, hyperalgesia, and motor dysfunction. Examples of the symptoms of peripheral neuropathic pain also include pains such as intense pain and burning pain, numbness of extremity ends, abnormal sensation such as burning sensation, hyperesthesia such as cold hypersensitivity, dysesthesia such as anesthesia, sensory paralysis, and discomfort, sensory ataxia, and reduction of muscle force. Allodynia usually means a symptom of sensing a stimulus that does not usually cause a pain (for example, light contact and pressure, or slight low temperature stimulus) as a pain. Allodynia caused by an anticancer agent include acute allodynia that appears immediately after administration of an anticancer agent, and chronic allodynia that appears in a delayed manner during continuation of treatment with an anticancer agent, and these types of allodynia are also encompassed within the scope of the peripheral neuropathic pain caused by an anticancer agent referred to in this embodiment. The acute allodynia is characteristic to oxaliplatin. As the diagnostic criteria of allodynia caused by an anticancer agent, DEB-NTC (Neurotoxicity Criteria of Debiopharm), CTCAE (Common Terminology Criteria for Adverse Events), and the like are used.

In this embodiment, allodynia as the peripheral neuropathic pain is not particularly limited so long as it is a symptom of sensing a stimulus as a pain that does not usually cause a pain. Examples include, for example, mechanical allodynia and cold allodynia, and mechanical allodynia is a preferred example. In another embodiment, cold allodynia may be preferred.

Examples of the mechanical allodynia include a symptom of sensing a touch stimulus as a pain that does not usually cause a pain. Examples include, for example, symptoms of difficulty in everyday actions such as fastening buttons of shirts, taking out coins in a purse, and walking.

Examples of the cold allodynia include a symptom of sensing a cold stimulus as a pain that does not usually cause a pain. Examples include, for example, symptoms of difficulty in such everyday actions as kitchen works and washing using water, holding a glass containing water, and going out in a winter season.

In this embodiment, thrombomodulin can be administered before an anticancer agent is administered (prophylactic administration), or can be administered after an anticancer agent is administered (therapeutic administration). It is preferable to administer it after an anticancer agent is administered. In another embodiment, it may be preferable to administer it before an anticancer agent is administered. Furthermore, thrombomodulin and an anticancer agent can also be simultaneously administered. As shown in Test Examples 1 mentioned later, administering thrombomodulin immediately before administering an anticancer agent or administering thrombomodulin simultaneously with administering an anticancer agent is one of preferred embodiments of the prophylactic administration.

Further, in both of the prophylactic administration and therapeutic administration, thrombomodulin can be administered during administration period of an anticancer agent.

From a viewpoint of continuity of the effect, the prophylactic administration is preferred. In other words, the medicament of this embodiment is preferably a medicament for prophylactic treatment of a peripheral neuropathic pain caused by an anticancer agent.

When thrombomodulin is administered before an anticancer agent is administered, the time from the administration of thrombomodulin to the administration of the anticancer agent is not particularly limited, so long as the effect of preventing peripheral neuropathic pain can be exhibited. Thrombomodulin is preferably administered 9 days, more preferably 7 days, still more preferably 5 days, further preferably 3 days, most preferably 1 day before the administration of the anticancer agent or thereafter. In another embodiment, it is most preferred that thrombomodulin is administered 12 hours before the administration of an anticancer agent or later therefrom. For example, thrombomodulin and a steroid for prophylaxis of an anaphylactic shock can be administered simultaneously, or they can be separately administered, before administration of an anticancer agent. Further, simultaneously with, before or after administration of an antiemetic agent, antiallergic agent, and/or anti-inflammatory agent, which is generally administered immediately before intravenous administration of an anticancer agent by drip infusion, thrombomodulin can be administered.

When thrombomodulin is administered after an anticancer agent is administered, the time from the administration of the anticancer agent to the administration of thrombomodulin is not particularly limited, so long as the effect of therapeutic treatment of peripheral neuropathic pain can be exhibited. Thrombomodulin is preferably administered 8 days, more preferably 6 days, still more preferably 4 days, particularly preferably 2 days, most preferably 6 hours, after the administration of the anticancer agent or earlier therefrom. In another embodiment, it is most preferred that thrombomodulin is administered 1 hour after the administration of an anticancer agent or earlier therefrom.

The medicament of this embodiment may contain a carrier. As the carrier usable in the present invention, a water-soluble carrier is preferred, and for example, the medicament of the present invention can be prepared by adding sucrose, glycerin, pH modifier consisting of an inorganic salt, or the like as additives. Further, if necessary, amino acids, salts, carbohydrates, surfactants, albumin, gelatin or the like may be added as disclosed in Japanese Patent Unexamined Publication Nos. (Hei)1-6219 and (Hei)6-321805, and it is also preferable to add a preservative. Preferred examples of preservative include parabenzoic acid esters, and a particularly preferred example is methyl parabenzoate. Amount of preservative to be added is usually 0.01 to 1.0% (in terms of weight %, the same shall apply to the following descriptions), preferably 0.1 to 0.3%. Method for adding these additives is not particularly limited. In the case of preparing a lyophilized product, examples of the method include, for example, a method of mixing a solution containing an anticancer agent and a solution containing thrombomodulin, and then adding additives to the mixture, and a method of mixing additives with an anticancer agent dissolved in water, water for injection, or an appropriate buffer beforehand, adding a solution containing thrombomodulin to the mixture, mixing the resulting mixture to prepare a solution, and lyophilizing the solution, in such manners as those commonly employed. When the medicament of the present invention is a medicament comprising a combination of components of the medicament, each component is preferably prepared by adding a carrier according to an appropriate preparation method. The medicament of this embodiment may be provided in the form of an injection, or in the form of a lyophilized preparation to be dissolved upon use.

Examples of the preparation method of the medicament include a method of filling a solution containing 0.05 to 15 mg/mL, preferably 0.1 to 5 mg/mL, of thrombomodulin, and the aforementioned additives in water for injection or an appropriate buffer in an ampoule or vial in a volume of, for example, 0.5 to 10 mL, freezing the solution, and drying the solution under reduced pressure. Such a solution, per se, can be prepared as an aqueous solution preparation for injection.

The medicament of the present invention is desirably administered by parenteral administration such as intravenous administration, intramuscular administration, and subcutaneous administration. The medicament may also be administered by oral administration, intrarectal administration, intranasal administration, sublingual administration or the like. When the medicament of the present invention is a medicament comprising a combination of multiple active ingredients, each active ingredient of the medicament is preferably administered by an administration method suitable for the ingredient.

Examples of method for the intravenous administration include a method of administering a desired dose of the medicament at one time, and intravenous administration by drip infusion.

The method of administering a desired dose of the medicament at one time (intravenous bolus administration) is preferred from the viewpoint that the method requires only a short time for administration. When the medicament is administered at one time, a period required for administration by using an injectable syringe may generally varies. In general, the period of time required for the administration is, for example, 5 minutes or shorter, preferably 3 minutes or shorter, more preferably 2 minutes or shorter, still more preferably 1 minute or shorter, particularly preferably 30 seconds or shorter, although it depends on a volume to be administered. Although the minimum administration time is not particularly limited, the period is preferably 1 second or longer, more preferably 5 seconds or longer, still more preferably 10 seconds or longer. The dose is not particularly limited so long that the dose is within the aforementioned preferred dose. Intravenous administration by drip infusion is also preferred from a viewpoint that blood level of thrombomodulin can be easily kept constant.

A daily dose of the medicament of the present invention may vary depending on age, body weight of patients, severity of disease, administration route and the like. In general, the maximum dose is preferably 20 mg/kg or less, more preferably 10 mg/kg or less, still more preferably 5 mg/kg or less, particularly preferably 2 mg/kg or less, and most preferably 1 mg/kg or less, and the minimum dose is preferably 0.001 mg/kg or more, more preferably 0.005 mg/kg or more, still more preferably 0.01 mg/kg or more, particularly preferably 0.02 mg/kg or more, and most preferably 0.05 mg/kg or more, in terms of the amount of thrombomodulin.

In the case of intravenous bolus administration, although the dose is not particularly limited so long as the dose is within the aforementioned preferred dose, the maximum daily dose is preferably 1 mg/kg or less, more preferably 0.5 mg/kg or less, still more preferably 0.1 mg/kg or less, particularly preferably 0.08 mg/kg or less, and most preferably 0.06 mg/kg or less, and the minimum dose is preferably 0.005 mg/kg or more, more preferably 0.01 mg/kg or more, still more preferably 0.02 mg/kg or more, and particularly preferably 0.04 mg/kg or more.

When the medicament of the present invention is administered to a patient having a body weight exceeding 100 kg, it may be preferably administered at a fixed dose of 6 mg, since blood volume is not proportional to the body weight, and blood volume is relatively reduced with respect to the body weight in such a patient.

In the case of continuous intravenous infusion, although the dose is not particularly limited so long as the dose is within the aforementioned preferred dose, the maximum daily dose is preferably 1 mg/kg or less, more preferably 0.5 mg/kg or less, still more preferably 0.1 mg/kg or less, particularly preferably 0.08 mg/kg or less, and most preferably 0.06 mg/kg or less, and the minimum dose is preferably 0.005 mg/kg or more, more preferably 0.01 mg/kg or more, still more preferably 0.02 mg/kg or more, and particularly preferably 0.04 mg/kg or more.

The medicament of this embodiment is not particularly limited, so long as the effect for the prophylactic and/or therapeutic treatment of a peripheral neuropathic pain caused by an anticancer agent can be confirmed after administration of thrombomodulin, and the effect is confirmed within, for example, 24 hours, preferably 12 hours, more preferably 6 hours, still more preferably 3 hours, particularly preferably 1 hour, most preferably 30 minutes, after administration of thrombomodulin. As described above, the medicament of this embodiment may sometimes be characterized in that the effect for the prophylactic and/or therapeutic treatment of a peripheral neuropathic pain caused by an anticancer agent can be confirmed at an early stage.

The medicament of this embodiment can be prescribed as a preparation for intermittent administration, or a preparation for continuous administration, and it is preferably prescribed as a preparation for intermittent administration.

The intermittent administration means to administer or release a medicament to or in the inside of the body once or more times, preferably two or more times, with a certain interval in a discontinuous manner. For example, the intermittent administration may be performed by administration of once or twice a day, and administration of once a day is preferred. Further, the intermittent administration may be performed by everyday administration, or administration on 1 to 3 days in a week, or administration on 1 to 5 days in a week, and administration on 1 day in a week is preferred. In another embodiment, administration on 5 days in a week may be preferred. In further another embodiment, everyday administration may be preferred.

Further, the intermittent administration may be performed by administration of once a day, once a week, 3 times a week, 5 times a week, or once in two weeks, and administration of once a week is preferred. In another embodiment, administration of 5 times in a week may be preferred. In further another embodiment, everyday administration may be preferred. Further, administration of once in two weeks may be preferred as the case may be.

The continuous administration means an administration method in which a medicament is continuously released in the inside of the body for a certain period of time, for example, at least 5 minutes or longer. So long as it is performed by systemic administration or local administration to a peripheral tissue, the administration route is not limited. Examples of administration or administration means include administration using instruments such as an infusion pump or transfusion pump, manual administration, sustained release preparations utilizing a polymer degradable in living bodies as a carrier, and the like.

The patient to be administered with the medicament of this embodiment is not particularly limited, so long as the patient is administered with an anticancer agent, and specific examples include cancer patients. Examples of the cancer patients include patients suffering from one or more kinds of cancers selected from the group consisting of, for example, ovarian cancer, non-small cell cancer, breast cancer, gastric cancer, endometrial cancer, head and neck cancer, esophageal carcinoma, leukemia, malignant lymphoma, pediatric tumor, multiple myeloma, malignant astrocytoma, neuroglioma, trophoblastic disease, germ cell tumor, lung cancer, orchioncus, vesical cancer, renal pelvic tumor, urethrophyma, prostate cancer, uterine cervix carcinoma, neuroblastoma, small cell lung cancer, osteosarcoma, malignant pleural mesothelioma, malignant osteoncus, and colon cancer.

The medicament of this embodiment can be administered together with one or more kinds of other medicaments used for treating peripheral neuropathies caused by anticancer agents, for example, one or two or more kinds of medicaments selected from steroids, antidepressants, antiepileptics, opioids, and the like, or can be prepared as a mixture with such one or two or more kinds of medicaments as mentioned above, and administered. Further, thrombomodulin may be administered with performing physiotherapy, complementary therapies such as massage and acupuncture, and the like.

Further, the present invention also provides a medicament for prophylactic and/or therapeutic treatment of a peripheral neuropathic pain caused by an anticancer agent, which is administered together with an anticancer agent, and contains thrombomodulin as an active ingredient. Examples of thrombomodulin used in this embodiment include the aforementioned preferred examples of soluble thrombomodulin. Further, examples of the anticancer agent used in this embodiment include the aforementioned preferred examples of the anticancer agent. Furthermore, examples of the peripheral neuropathic pain referred to in this embodiment include the aforementioned preferred examples of peripheral neuropathic pain.

The present invention further provides a medicament for prophylactic and/or therapeutic treatment of a peripheral neuropathic pain caused by an anticancer agent, which comprises thrombomodulin and an anticancer agent as active ingredients.

Furthermore, a method for prophylactic and/or therapeutic treatment of a peripheral neuropathic pain caused by an anticancer agent, which comprises the step of administering thrombomodulin to a mammal also falls within the scope of the present invention.

Furthermore, use of thrombomodulin for manufacturing a medicament for prophylactic and/or therapeutic treatment of a peripheral neuropathic pain caused by an anticancer agent also falls within the scope of the present invention.

EXAMPLES

The present invention will be explained in detail with reference to test examples and examples. However, the present invention is not limited by these examples at all.

EXPLANATION OF SEQUENCE LISTING

SEQ ID NO: 1: Amino acid sequence encoded by the gene used in production of TME456
SEQ ID NO: 2: Nucleotide sequence encoding the amino acid sequence of SEQ ID NO: 1
SEQ ID NO: 3: Amino acid sequence encoded by the gene used in production of TME456M
SEQ ID NO: 4: Nucleotide sequence encoding the amino acid sequence of SEQ ID NO: 3
SEQ ID NO: 5: Amino acid sequence encoded by the gene used in production of TMD12
SEQ ID NO: 6: Nucleotide sequence encoding the amino acid sequence of SEQ ID NO: 5
SEQ ID NO: 7: Amino acid sequence encoded by the gene used in production of TMD12M
SEQ ID NO: 8: Nucleotide sequence encoding the amino acid sequence of SEQ ID NO: 7
SEQ ID NO: 9: Amino acid sequence encoded by the gene used in production of TMD123
SEQ ID NO: 10: Nucleotide sequence encoding the amino acid sequence of SEQ ID NO:
SEQ ID NO: 11: Amino acid sequence encoded by the gene used in production of TMD123M
SEQ ID NO: 12: Nucleotide sequence encoding the amino acid sequence of SEQ ID NO: 11
SEQ ID NO: 13: Synthetic DNA for mutation used for carrying out site-directed mutagenesis The thrombomodulin of the present invention used in the test examples was prepared according to the aforementioned method of Yamamoto et al. (the method described in Japanese Patent Unexamined Publication No. 64-6219). Preparation examples thereof are described below. Safety of the thrombomodulins obtained in these preparation examples was confirmed by single and repetitive intravenous administration tests using rats and monkeys, mouse reproduction test, local irritation test, pharmacological safety test, virus inactivation test, and the like.

Preparation Example 1

<Obtaining Thrombomodulin>

A highly purified product was obtained by the aforementioned method. Specifically, Chinese hamster ovary (CHO) cells were transfected with a DNA encoding the amino acid sequence of SEQ ID NO: 9 (which specifically consisted of the nucleotide sequence of SEQ ID NO: 10). From the culture of the above transformant cells, a highly purified product was obtained by collecting an active fraction with a 20 mmol/L phosphate buffer (pH 7.3) containing 50 mmol/L NaCl according to the aforementioned conventional purification method. The product was further concentrated by ultrafiltration to obtain a thrombomodulin solution having a concentration of 11.2 mg/mL (henceforth also abbreviated as TMD123 in the specification).

<Preparation of Additive Solution>

Arginine hydrochloride (480 g, Ajinomoto) was weighed, put into a 10-L volume stainless steel vessel, added with water for injection (5 L), and dissolved. The solution was adjusted to pH 7.3 by adding a 1 mol/L sodium hydroxide solution.

<Preparation and Filling of Drug Solution>

The total volume of the additive solution obtained above was put into a 20-L stainless steel vessel, and added with the TMD123 solution obtained above (2398 mL, corresponding to 26.88 g of soluble thrombomodulin protein, added in a 12% excess amount), and the mixture was stirred. The mixture was further added with water for injection to obtain a total volume of 12 L, and the mixture was made uniform by stirring. This drug solution was subjected to filtration sterilization using a filter having a pore diameter of 0.22 μm (MCGL10S, manufactured by Millipore). The filtrate was filled in vials in a volume of 1 mL each, and the vials were half-closed with rubber stoppers.

<Lyophilization>

A lyophilization step was performed under the following conditions in the order of lyophilization→filling nitrogen-→complete closing with rubber stopper→screwing cap to obtain a TMD123-containing preparation containing 2 mg of soluble thrombomodulin and 40 mg of arginine hydrochloride in one vial.

<Lyophilization Conditions>

Preliminary cooling (from room temperature to 15° C. over 15 minutes)→main cooling (from 15° C. to −45° C. over 2 hours)→retention (−45° C. for 2 hours)→start of vacuuming (−45° C. for 18 hours)→temperature increase (from −45° C. to 25° C. over 20 hours)→retention (25° C. for 15 hours)→temperature increase (from 25° C. to 45° C. over 1 hour)→retention (45° C. for 5 hours)→room temperature (from 45° C. to 25° C. over 2 hours)→pressure recovery and nitrogen filling (up to −100 mmHg)→complete closure with stopper→screwing cap Preparation Example 2

Chinese hamster ovary (CHO) cells are transfected with a DNA encoding the amino acid sequence of SEQ ID NO: 11 (which specifically consists of the nucleotide sequence of SEQ ID NO: 12), a solution of thrombomodulin purified from a culture of the above transformant cells (henceforth also abbreviated as TMD123M in the specification) by the aforementioned conventional purification method is obtained, and a Lyophilized TMD123M preparation is obtained in the same manner as that described above.

Preparation Example 3

Chinese hamster ovary (CHO) cells are transfected with a DNA encoding the amino acid sequence of SEQ ID NO: 1 (which specifically consists of the nucleotide sequence of SEQ ID NO: 2), thrombomodulin purified from a culture of the above transformant cells (henceforth also abbreviated as TME456 in the specification) by the aforementioned conventional purification method is obtained, and a Lyophilized TME456 preparation is obtained in the same manner as that described above.

Preparation Example 4

Chinese hamster ovary (CHO) cells are transfected with a DNA encoding the amino acid sequence of SEQ ID NO: 3 (which specifically consists of the nucleotide sequence of SEQ ID NO: 4), thrombomodulin purified from a culture of the above transformant cells (henceforth also abbreviated as TME456M in the specification) by the aforementioned conventional purification method is obtained, and a Lyophilized TME456M preparation is obtained in the same manner as that described above.

Preparation Example 5

Chinese hamster ovary (CHO) cells are transfected with a DNA encoding the amino acid sequence of SEQ ID NO: 5 (which specifically consists of the nucleotide sequence of SEQ ID NO: 6), thrombomodulin purified from a culture of the above transformant cells (henceforth also abbreviated as TMD12 in the specification) by the aforementioned conventional purification method is obtained, and a Lyophilized TMD12 preparation is obtained in the same manner as that described above.

Preparation Example 6

Chinese hamster ovary (CHO) cells are transfected with a DNA encoding the amino acid sequence of SEQ ID NO: 7 (which specifically consists of the nucleotide sequence of SEQ ID NO: 8), thrombomodulin purified from a culture of the above transformant cells (henceforth also abbreviated as TMD12M in the specification) by the aforementioned conventional purification method is obtained, and a Lyophilized TMD12M preparation is obtained in the same manner as that described above.

Test Example 1

Action on Mouse Allodynia Induced by Paclitaxel

In order to confirm the effect of thrombomodulin on allodynia caused by an anticancer agent, action of thrombomodulin on allodynia caused by a mechanical stimulus generated when an anticancer agent, paclitaxel, is administered to a mouse was investigated. TMD123 as a test drug was intraperitoneally administered to mice, and the following test was performed.

(1) Preparation of Paclitaxel Administration-Induced Allodynia Model Mice

As experimental animals, 4 to 5 week-old ddY male mice (20 to 30 g) were used, and 4 mg/kg of paclitaxel (henceforth also abbreviated as PTX) was intraperitoneally administered to the mice. The administration was performed 4 times in total every other day (days 0, 2, 4 and 6). To the control group mice, 0.5 mL of the solvent of PTX, i.e., a 1:1 mixed solution of Cremophor EL and ethanol, diluted to 1.5 mL with physiological saline was similarly administered.

As the paclitaxel, Paclitaxel (100 mg, LKT Laboratories, Inc.) was used.

(2) Administration of Test Drug

In the experiment for evaluating prophylactic effect, the experimental animals consisted of 5 groups, i.e., a control group, a PTX administration group, and PTX and 0.1, 1, or 10 mg/kg thrombomodulin administration groups (PTX+TM administration groups). In the experiment for evaluating the therapeutic effect, the experimental animals consisted of two groups, i.e., a PTX administration group, and a PTX and 10 mg/kg thrombomodulin administration group (PTX+TM administration group). In the prophylactic treatment experiment, TMD123, which is thrombomodulin, was intraperitoneally administered to the mice of the PTX+TM administration group once a day for 7 days from the day of the start of the PTX administration. Further, in the therapeutic treatment experiment, TMD123 was intraperitoneally administered single time 8 or 9 days after the final start of PTX administration. To the mice of the control group and the PTX administration group, the solvent of TMD123 was similarly administered.

(3) Statistical Analysis

The statistical analysis of the results were performed by using the Wilcoxon test for comparison of two groups, and the Kruskal-Wallis H test and the LSD (least significant difference)-type test for comparison of three or more groups, and a critical rate of 5% or smaller was determined to indicate presence of significant difference. The meanings of the symbols used in the graphs are as follows.

*, , and *: Comparison of the measured values for the control group and the PTX administration group, the symbols represent $p<0.05$, $p<0.01$, and $p<0.001$, respectively † and †††: Comparison of the measured values for the PTX administration group and the PTX and test drug administration group, the symbols represent $p<0.05$, and $p<0.001$, respectively (4) Von Frey Test Pain threshold values of the aforementioned mice were measured by the up-down method using von Frey filaments. Namely, von Frey filaments for strengths of 0.008, 0.02, 0.04, 0.07, 0.16, 0.4, 0.6, and 1.0 g were used to continuously stimulated hind paw soles of the mice for 6 seconds, and reactions of the mice such as raising, shaking, and licking the stimulated legs were observed. The stimulating was started with a smaller strength, and when there was not observed any reaction, stimulation was given again at a one-rank higher strength. When a reaction was observed, stimulation was given at a one-rank lower strength after an interval of 30 seconds or longer. The stimulating was repeated 5 times from the first reaction after starting the stimulating, and the strength of the filament to which 50% of the mice showed reactions was determined as the nociceptive threshold value.

The baseline threshold value was measured before the PTX administration, and then the pain threshold value was measured on the PTX administration day, and day 8 or 9 after the start of the administration for follow-up. In the therapeutic treatment experiment, on the day 8 or thereafter, sufficient reduction of the pain threshold value was confirmed, and then the measurement test was performed.

As the results of the aforementioned test (up-down method using von Frey filaments), the results of the prophylactic administration of TMD123 are shown in FIG. 1, and the results of the therapeutic administration of TMD123 are shown in FIG. 2. The pain threshold value (Threshold) significantly decreased in the PTX administration group compared with the control group, whilst such decrease of the threshold value observed in the PTX administration group was significantly suppressed in the PTX+TM prophylactic administration group. Further, in the PTX+TM therapeutic administration group, the threshold value, which was decreased by the PTX administration, was significantly increased from 30 minutes after the administration, and maintained over 3 hours or more after the administration.

On the basis of the aforementioned results, it was revealed that thrombomodulin has prophylactic and/or therapeutic effect against mechanical allodynia induced by PTX with superior fast-acting property and sustainability.

Test Example 2

Cold Stimulation Test 1 (Cold Plate Test)

By observing allodynia induced by cold stimulation according to the method shown below, the effect of the present invention on a peripheral neuropathic pain caused by an anticancer agent can be verified.
(1) Preparation of Paclitaxel Administration-Induced Allodynia Model Rats As experimental animals, 5 week-old SD male rats (150 to 200 g) are used, and 4 mg/kg of PTX is intraperitoneally administered to the rats. The administration is performed 4 times in total every other day (days 0, 2, 4 and 6). To the control group rats, 0.5 mL of the solvent of PTX, i.e., a 1:1 mixed solution of Cremophor EL and ethanol, diluted to 1.5 mL with physiological saline is similarly administered.
(2) Administration of Test Drug The experimental animals consist of three groups, i.e., a control group, a PTX administration group, and a PTX and thrombomodulin administration groups (PTX+TM administration group). To the PTX+TM administration group rats, TMD123, which is thrombomodulin, is intraperitoneally administered once a day for 7 days (10 mg/kg) from the day of the start of the PTX administration as prophylactic administration, and intraperitoneally administered single time (10 mg/kg) on the next day of the final administration of PTX as therapeutic administration. To the rats of the control group and the PTX administration group, the solvent of TMD123 was similarly administered.
(3) Cold Plate Test By measuring latent times for evasive actions after stimuli are given 5 times alternately to soles of right and left hind feet of the rats of the aforementioned 5 groups using a tip of a cold stimulation part of a cold sensing threshold value analysis device, which is controlled to be at 8° C., to observe allodynia induced by cold stimulation, the effect of the present invention on peripheral neuropathic pain caused by an anticancer agent can be confirmed. The cut off time is, for example, 15 seconds. The measurement test can be performed at the times 5 hours before the PTX administration, 1 hour after the PTX administraiont, 2, 3, 5, 7, 9, and 11 days after the PTX administration, 15 days after the PTX administration and before the test drug administration, 15 days after the PTX administration and 6 hours after the test drug administration, 17 and 19 days after the PTX administration and before the test drug administration, 22 days after the PTX administration and after 3 days of drug withdrawal period, 26 days after the PTX administration and after 7 days of drug withdrawal period, and 29 days after the PTX administration and after 10 days of drug withdrawal period.

The experimental conditions can be appropriately changed.

Test Example 3

Cold Stimulation Test 2

By using rats administered with PTX in the same manner as that of Test Example 2, and observing allodynia induced by cold stimulation according to the method described below, the effect of the present invention on peripheral neuropathic pain caused by an anticancer agent can also be confirmed.

Rats are put into a cage having a wire gauze bottom, and acclimated for 1 hour, and then 0.05 mL of acetone is sprayed on the hind legs over 5 seconds by using MicroSprayer (PENN-Century) to give cold stimulation by utilizing the cooling action generated at the time of vaporization of acetone. Avoidance reactions of the rats are observed for 40 seconds from the start of the spraying, and times until they reacted (latent times) are recorded. The test is performed 3 times for each of the right and left legs, and average is calculated. The measurement can be performed at the times 5 hours before the PTX administration, 1 hour after the PTX administration, 2, 3, 5, 7, 9, and 11 days after the PTX administration, 15 days after the PTX administration and before the test drug administration, 15 days after the PTX administration and 6 hours after the test drug administration, 17 and 19 days after the PTX administration and before the test drug administration, 22 days after the PTX administration and after 3 days of drug withdrawal period, 26 days after the PTX administration and after 7 days of drug withdrawal period, and 29 days after the PTX administration and after 10 days of drug withdrawal period.

The experimental conditions can be appropriately changed.

Test Example 4

Action on Rat Allodynia Induced by Oxaliplatin

In the same manner as those of Test Examples 1 to 3, the von Frey test and cold stimulation test are performed with oxaliplatin administration by using rats. The effect of the present invention on peripheral neuropathic pain caused by an anticancer agent can be confirmed by these test examples.

Test Example 5

In Vitro Denaturation of Nerve Cells

By the following method, effect of the peripheral neuropathy-relieving action of the present invention can be confirmed.

In order to examine the action on nerve cell denaturation induced by a treatment with paclitaxel, the rat suprarenal gland pheochromocytoma 12 (PC12) cells and dorsal root ganglia (DRG) cells, which are model cell lines of nerve differentiation and neurite extension, are used.

(1) Culture of Cells

The PC12 cells are cultured at 37° C. in a 5% $CO_2$ incubator by using the RPMI1640 medium (MP Biomedicals) containing 5% fetal bovine serum, 10% horse serum, and 100 units/mL of penicillin/streptomycin (Gibco BRL). The DRG cells are extracted from an SD male rat and cultured as primary culture, and then 5 nodes of DRG of L4 and L5 were treated with collagenase type I (Funakoshi), and dispase I (Sanko Junyaku), inoculated on a 24-well plate, and further cultured. The culture is performed at 37° C. in a 5% $CO_2$ incubator by using the Dulbecco's modified Eagle's medium (DMEM medium, MP Biomedical) containing 10% fetal bovine serum and 100 units/mL of penicillin/streptomycin.

(2) Drug Treatment and Measurement of Neurite Length

The PC12 cells are inoculated on a 24-well plate at a density of 10,000 cells/well, then after 3 hours, the cells are treated with 0.01 mmol/L of Fos-Choline to allow neurite extension, and after 24 hours, the cells are treated with a test solution. The DRG cells are cultured for one week, and after confirming cell adhesion and neurite extension, they are treated with a test solution. As the test solution, only a 10 ng/mL paclitaxel solution is added, or a solution of 10 ng/mL of paclitaxel and a test drug (10 ng/mL to 0.1 mg/mL) is added. After 24 and 96 hours from the treatment with a test solution, the medium is exchanged with a fresh medium containing the test drug, and after 168 hours, only dead cells are stained with a trypan blue staining solution, and the cells are photographed with a light microscope (magnification, 200 times; 3 views/well). After the photographing, lengths of the neurites of live cells are measured with the analysis software Image J.

The experimental conditions can be appropriately changed.

Test Example 6

Action on Rat Allodynia Induced by Paclitaxel

In the same manner as that of Test Example 1, action of thrombomodulin on allodynia induced by mechanical stimulation generated when the anticancer agent, paclitaxel, was administered to rats was investigated by the method described below. TMD123 as the test drug was intraperitoneally administered to rats, and the following test was performed.

(1) Preparation of Paclitaxel Administration-Induced Allodynia Model Rats

As experimental animals, 5 to 6 week-old Wistar male rats (200 to 250 g) were used, and 2 mg/kg of PTX was intraperitoneally administered to the rats. The administration was performed 4 times in total every other day (days 0, 2, 4 and 6). To the control group rats, 0.5 mL of the solvent of PTX, i.e., a 1:1 mixed solution of Cremophor EL and ethanol, diluted to 1.5 mL with physiological saline was similarly administered.

(2) Administration of Test Drug

In the experiment for evaluating prophylactic effect using the rats, the experimental animals consisted of three groups, i.e., a control group, a PTX administration group, and a PTX and 10 mg/kg thrombomodulin administration group (PTX+TM administration group). As prophylactic administration, TMD123, which is thrombomodulin, was intraperitoneally administered to the rats once a day for 7 days (10 mg/kg) from the day of the start of the PTX administration.

(3) Statistical Analysis

The statistical analysis of the results was performed by using the Kruskal-Wallis H test and the LSD (least significant difference)-type test, and a critical rate of 5% or smaller was determined to indicate presence of significant difference. The meanings of the symbols used in the graphs are as follows.

* and **: Comparison of the measured values for the control group and the PTX administration group, the symbols represent $p<0.05$, and $p<0.01$, respectively † and ††: Comparison of the measured values for the PTX administration group and the PTX and test drug administration group, the symbols represent $p<0.05$, and $p<0.01$, respectively.

(4) Randall-Selitto Test

The aforementioned rats were subjected to a measurement based on the paw pressure test described in Randall L O. et al., Arch. Int. Pharmacodyn. Ther., 1957, 111, 409-419 (Randall-Selitto test). Namely, the right hind paw was gradually increasingly pressurized with a pressure stimulation analgesic effect analyzer, and the pressure at which each rat showed an abnormal phonation reaction or escape reaction was determined as the pain threshold value.

The results of the test for prophylactic administration of TMD123 using rats are shown in FIG. 3. Whereas the pain threshold value (Threshold) was significantly reduced in the PTX administration group compared with the control group, such decrease of the threshold value observed in the PTX administration group was significantly suppressed in the PTX+TM administration group. Further, in the test by using rats, the decrease of the threshold value observed in the PTX administration group was significantly suppressed in the PTX+TM administration group over 28 days.

On the basis of the above results, it was revealed that thrombomodulin shows prophylactic effect against mechanical allodynia induced by PTX with superior fast-acting property and sustainability.

Test Example 7

Prophylactic Effect on Peripheral Neuropathic Pain Caused by an Anticancer Agent in Human For example, when chemotherapy of 12 courses, each of which consists of two weeks, are performed with FOLFOX™6, mFOLFOX™6, or the like for a patient with a malignant tumor such as colon cancer, TMD3123 (for example, Recomodulin (registered trademark), Asahi Kasei Pharma Corporation) is administered to the patient immediately before, during, or immediately after the administration of the anticancer agent in each course, After completion of the chemotherapy, by investigating drop out rate of the chemotherapy, incidence rate of peripheral neuropathic pain, QOL, change of laboratory data of coagulation study, effect on the tumor, and the like, the prophylactic effect of the present invention on peripheral neuropathic pain caused by an anticancer agent in human can be confirmed.

The type of the anticancer agent, doses of the anticancer agent and TMD123, administration timing, length of the course, number of the course, and the like can be appropriately changed in light of common technical knowledge.

INDUSTRIAL APPLICABILITY

The medicament of the present invention is extremely effective for prophylactic and/or therapeutic treatment of a peripheral neuropathic pain caused by an anticancer agent, and can significantly improve quality of life of patients, which is markedly degraded by a peripheral neuropathic pain caused by a treatment with an anticancer agent. Therefore, the medicament of the present invention is useful in the field of pharmaceutical industry.

What is claimed is:

1. A method for treating chemotherapy-induced peripheral neuropathic pain caused by paclitaxel, docetaxel, oxaliplatin, or nedaplatin in a cancer patient, which comprises:
    administering paclitaxel, docetaxel, oxaliplatin or nedaplatin to the patient; and
    administering thrombomodulin to the patient between 12 hours before and 6 hours after the administration of the paclitaxel, docetaxel, oxaliplatin or nedaplatin to the patient.

2. The method according to claim 1, wherein paclitaxel is administered.

3. The method according to claim 1, wherein oxaliplatin is administered.

4. The method according to claim 1, wherein said thrombomodulin is administered to the patient intravenously.

5. The method according to claim 1, wherein said thrombomodulin is administered to the patient subcutaneously.

6. The method according to claim 1, wherein said thrombomodulin is administered to the patient at a dose of 0.04-0.08 mg/kg/day.

7. The method according to claim 1, wherein said thrombomodulin is administered before paclitaxel, docetaxel, oxaliplatin or nedaplatin is administered.

8. The method according to claim 1, wherein said thrombomodulin is administered after paclitaxel, docetaxel, oxaliplatin or nedaplatin is administered.

9. The method according to claim 8, wherein said thrombomodulin is administered within 1 hour after paclitaxel, docetaxel, oxaliplatin or nedaplatin is administered.

10. The method according to claim 1, wherein said thrombomodulin is administered simultaneously with paclitaxel, docetaxel, oxaliplatin or nedaplatin.

11. The method according to claim 1, wherein the thrombomodulin is a soluble thrombomodulin.

12. The method according to claim 11, wherein the thrombomodulin is a human soluble thrombomodulin.

13. The method according to claim 1, wherein the peripheral neuropathic pain is one or more kinds of symptoms selected from the group consisting of numbness of extremities, pain of extremities, reduction of deep tendon reflection, reduction of muscle force, allodynia, hyperalgesia, and motor dysfunction.

14. The method according to claim 1, wherein the peripheral neuropathic pain is allodynia.

15. The method according to claim 14, wherein the allodynia is mechanical allodynia.

16. The method according to claim 1, wherein the patient is suffering from one or more kinds of cancers selected from the group consisting of ovarian cancer, non-small cell cancer, breast cancer, gastric cancer, endometrial cancer, head and neck cancer, esophageal carcinoma, leukemia, malignant lymphoma, pediatric tumor, multiple myeloma, malignant astrocytoma, neuroglioma, trophoblastic disease, germ cell tumor, lung cancer, orchioncus, vesical cancer, renal pelvic tumor, urethrophyma, prostate cancer, uterine cervix carcinoma, neuroblastoma, small cell lung cancer, osteosarcoma, malignant pleural mesothelioma, malignant osteoncus, and colon cancer, and wherein the patient is a human cancer patient.

17. The method according to claim 1, wherein the thrombomodulin is a peptide obtainable from a transformed cell prepared by transfecting a host cell with a DNA coding for the amino acid sequence of (i-1) or (i-2) mentioned below, and the peptide is a peptide having the thrombomodulin activities;
(i-1) the amino acid sequence of SEQ ID NO: 9 or 11, or
(i-2) the amino acid sequence of (i-1) mentioned above, further including substitution, deletion or addition of one or more amino acid residues.

18. The method according to claim 1 wherein the thrombomodulin is a peptide containing the amino acid sequence of (i-1) or (i-2) mentioned below, and the peptide is a peptide having the thrombomodulin activities;
(i-1) the amino acid sequence of the positions 19 to 516 in the amino acid sequence of SEQ ID NO: 9 or 11, or
(i-2) the amino acid sequence of (i-1) mentioned above, further including substitution, deletion or addition of one or more amino acid residues.

19. A method for treating chemotherapy-induced peripheral neuropathic pain caused by paclitaxel, docetaxel, oxaliplatin, or nedaplatin in a cancer patient, which comprises:
administering paclitaxel, docetaxel, oxaliplatin, or nedaplatin to the patient; and
administering thrombomodulin to the patient, wherein the administration of paclitaxel, docetaxel, oxaliplatin, or nedaplatin is within 8 days of the administration of thrombomodulin.

20. The method of claim 19, wherein the administration of thrombomodulin is 3 days or less before the administration of paclitaxel, docetaxel, oxaliplatin, or nedaplatin.

21. The method of claim 19, wherein the administration of thrombomodulin is 1 day or less before the administration of paclitaxel, docetaxel, oxaliplatin, or nedaplatin.

22. The method of claim 19, wherein the administration of thrombomodulin is 12 hours or less before the administration of paclitaxel, docetaxel, oxaliplatin, or nedaplatin.

23. A method for treating chemotherapy-induced peripheral neuropathic pain caused by paclitaxel, docetaxel, oxaliplatin, or nedaplatin in a cancer patient, which comprises:
administering paclitaxel, docetaxel, oxaliplatin or nedaplatin to the patient; and
administering thrombomodulin to the patient,
wherein said method does not further comprise hematopoietic cell transplantation.

24. The method according to claim 23, wherein said thrombomodulin is administered before paclitaxel, docetaxel, oxaliplatin or nedaplatin is administered.

25. The method according to claim 23, wherein said thrombomodulin is administered within 12 hours before paclitaxel, docetaxel, oxaliplatin or nedaplatin is administered.

26. The method according to claim 23, wherein said thrombomodulin is administered after paclitaxel, docetaxel, oxaliplatin or nedaplatin is administered.

27. The method according to claim 23, wherein said thrombomodulin is administered simultaneously with paclitaxel, docetaxel, oxaliplatin or nedaplatin.

28. The method according to claim 23, wherein the thrombomodulin is a human soluble thrombomodulin.

29. The method according to claim 23, wherein said thrombomodulin is administered after an anticancer agent is administered.

30. The method according to claim 23, wherein said thrombomodulin is administered simultaneously with an anticancer agent.

31. A method for treating chemotherapy-induced peripheral neuropathic pain caused by an anticancer agent in a cancer patient, which comprises:
administering an anticancer agent to the patient; and
administering thrombomodulin to the patient between 12 hours before and 6 hours after the administration of an anticancer agent to the patient.

32. A method for treating chemotherapy-induced peripheral neuropathic pain caused by an anticancer agent in a cancer patient, which comprises:
administering an anticancer agent to the patient; and
administering thrombomodulin to the patient, wherein the administration of an anticancer agent is within 8 days of the administration of thrombomodulin.

33. The method of claim 32, wherein the administration of thrombomodulin is 1 day or less before the administration of an anticancer agent.

34. The method of claim 32, wherein the administration of thrombomodulin is 12 hours or less before the administration of an anticancer agent.

35. A method for treating chemotherapy-induced peripheral neuropathic pain caused by an anticancer agent in a cancer patient, which comprises:
administering an anticancer agent to the patient; and
administering thrombomodulin to the patient,
wherein said method does not further comprise hematopoietic cell transplantation.

36. The method according to claim 35, wherein said thrombomodulin is administered before an anticancer agent is administered.

37. The method according to claim 35, wherein said thrombomodulin is administered within 12 hours before an anticancer agent is administered.

38. The method according to claim 31, 33 or 35 wherein the anticancer agent is a taxane drug or a platinum preparation.

39. The method according to claim 31, 33 or 35 wherein the thrombomodulin is a peptide obtainable from a transformed cell prepared by transfecting a host cell with a DNA coding for the amino acid sequence of (i-1) or (i-2) mentioned below, and the peptide is a peptide having the thrombomodulin activities;
(i-1) the amino acid sequence of SEQ ID NO: 9 or 11, or
(i-2) the amino acid sequence of (i-1) mentioned above, further including substitution, deletion or addition of one or more amino acid residues.

40. The method according to claim 31, 33 or 35 wherein the thrombomodulin is a peptide containing the amino acid sequence of (i-1) or (i-2) mentioned below, and the peptide is a peptide having the thrombomodulin activities;
(i-1) the amino acid sequence of the positions 19 to 516 in the amino acid sequence of SEQ ID NO: 9 or 11, or
(i-2) the amino acid sequence of (i-1) mentioned above, further including substitution, deletion or addition of one or more amino acid residues.

* * * * *